(12) United States Patent
Song et al.

(10) Patent No.: US 8,178,100 B2
(45) Date of Patent: May 15, 2012

(54) ANTIBODIES TO IP-10 FOR TREATING BONE DISEASES WITH BONE DESTRUCTION

(75) Inventors: Young Wook Song, Seoul (KR); Zang Hee Lee, Seoul (KR); Eun Bong Lee, Seoul (KR); Eun Young Lee, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 270 days.

(21) Appl. No.: 12/311,786

(22) PCT Filed: Aug. 17, 2007

(86) PCT No.: PCT/KR2007/003935
§ 371 (c)(1), (2), (4) Date: Apr. 13, 2009

(87) PCT Pub. No.: WO2008/044824
PCT Pub. Date: Apr. 17, 2008

(65) Prior Publication Data
US 2010/0021463 A1    Jan. 28, 2010

(30) Foreign Application Priority Data
Oct. 13, 2006 (KR) .................. 10-2006-0099954

(51) Int. Cl.
*A61K 39/395* (2006.01)
*C07K 16/24* (2006.01)
(52) U.S. Cl. .................. 424/145.1; 530/388.23
(58) Field of Classification Search .......... None
See application file for complete search history.

(56) References Cited

U.S. PATENT DOCUMENTS 6,998,383 B2   2/2006 Aggarwal et al.
2005/0053600 A1*  3/2005 Lane .................. 424/141.1

FOREIGN PATENT DOCUMENTS

WO  WO 2005/023201   3/2005
WO  WO 2005/058815   6/2005

OTHER PUBLICATIONS van Bezooijen et al. Sclerostin is an osteocyte-expressed negative regulator of bone formation, but not a classical BMP antagonist. J Exp Med. Mar. 15, 2004;199(6):805-14.*
Kwak et al., "Monokine Induced by Interferon-{gamma} is Induced by Receptor Activator of Nuclear Factor {kappa}B Ligand and is Involved in Osteoclast Adhesion and Migration," Blood 105:2963-2969, 2005.
Taubman et al., "Involvement of T-Lymphocytes in Periodontal Disease and in Direct and Indirect Induction of Bone Resorption," Crt. Rev. Oral Biol. Med. 12:125-135, 2001.
International Search Report from International Application No. PCT/KR2007/003935, dated Dec. 28, 2007.

* cited by examiner

*Primary Examiner* — David Romeo
(74) *Attorney, Agent, or Firm* — Clark & Elbing LLP

(57) ABSTRACT

The present invention is directed to providing the IP-10 protein (interferon-γ-inducible protein 10) as a novel therapeutic target relating to the etiology of bone diseases with bone destruction associated with RNAKL expression and osteoclast formation. More specifically, the present invention relates to (i) a pharmaceutical composition for preventing or treating a disease or disorder associated with the expression of RANKL (receptor activator of NF-κB ligand), (ii) a method for inhibiting the expression of RANKL and (iii) a method for screening an antibody drug candidate to inhibit the expression of RANKL.

5 Claims, 11 Drawing Sheets
(5 of 11 Drawing Sheet(s) Filed in Color)

ANTIBODIES TO IP-10 FOR TREATING BONE DISEASES WITH BONE DESTRUCTION

CROSS-REFERENCE TO RELATED APPLICATIONS

This application claims priority under 35 U.S.C. §371 from international application PCT/KR2007/003935, filed Aug. 17, 2007, which claims priority from Korean Patent Application 10-2006-0099954, filed Oct. 13, 2006.

BACKGROUND OF THE INVENTION

1. Field of the Invention

The present invention relates to a pharmaceutical composition for preventing or treating a disease or disorder associated with the expression of RANKL (receptor activator of NF-κB ligand), a method for inhibiting the expression of RANKL and a method for screening an antibody drug candidate to inhibit the expression of RANKL.

2. Description of the Related Art

The regulation of osteoclasts is vital for maintaining the balance in bone remodeling, i.e., bone resorption by osteoclasts and bone formation by osteoblasts, and thus is important in the treatment of bone disease. Bone-resorbing osteoclasts are derived from hematopoietic cells of the monocyte-macrophages lineage and differentiate into multinucleated cells through multiple processes.[1,2] Osteoclast formation and activity are regulated by local factors and by stromal and osteoblast cells in the bone environment.[3] Increases in osteoclast number and activity can be caused by systemic alterations, such as the up-regulation of osteotropic or osteoclastogenic factors or a deficiency of estrogen, and in turn cause bone disease, including rheumatoid arthritis (RA), periodontal disease, and osteoporosis.[4,5] In particular, receptor activator of NF-κB ligand (RANKL), a member of the TNF family that is expressed on stromal and osteoblast cells, plays an essential role in osteoclast differentiation and function. Several inflammatory cytokines including TNF-α and IL-1 can induce RANKL expression on stromal and osteoblast cells, which plays an important role in the bone and cartilage destruction in RA.[6] Thus, the regulation of RANKL expression is important for preventing bone disorders caused by increased osteoclast formation.

Chemokines are a superfamily of cytokines important in inflammation and immune responses. Chemokines can be divided into four main groups (C, CC, CXC, and $CX_3C$) according to the presence of none, one, or three amino acids between the first two cysteine residues, respectively.[7,8] Several chemokines promote bone resorption by inducing osteoclast formation and survival as well as by directly inducing the migration and adhesion of leukocytes.[9,10] In particular, the expression of MIP-1α and MIP-1β in multiple myeloma cells enhances osteolytic lesions by enhancing osteoclast formation and bone resorption.[11] IFN-γ-inducible protein 10 (IP-10) was initially identified as a chemokine induced by IFN-γ that is secreted by various cell types.[12] IFN stimulus response element and κB sites in the IP-10 promoter are important for IFN-γ-induced expression.[13] IP-10 binds the receptor CXCR3 (CXC chemokine receptor 3) and regulates immune responses through activation and recruitment of leukocytes, including T cells, eosinophils, and monocytes.[14,15] Also, IP-10 has antitumor activity in vivo, which has been attributed to the recruitment of lymphocytes. However, the role of IP-10 in the aspect of bone resorption has not yet been reported.

RA, a chronic inflammatory disease, is characterized by excessive bone resorption in the inflamed joints that is initially promoted through the recruitment of activated T cells.[16] Although it has been reported that many chemokines and inflammatory cytokines induce the infiltration of inflammatory cells into the synovium of inflamed joints and mediate inflammation,[17,19] the etiology of RA remains unknown. IP-10-deficient mice do not respond to allogeneic or antigenic stimulation and have defective trafficking of T cells.[20] IP-10 is expressed in many T cell-related inflammatory diseases, such as multiple sclerosis, atherosclerosis, and lichen planus.[21-23] Furthermore, a recent study by Hanaoka et al. showed that IP-10 is elevated in the synovial fluids of RA patients.[24] These results suggest that IP-10 plays an important role in T cell-related inflammation and in the recruitment of T cells to inflammatory sites.

Throughout this application, various patents and publications are referenced and citations are provided in parentheses. The disclosure of these patents and publications in their entireties are hereby incorporated by references into this application in order to more fully describe this invention and the state of the art to which this invention pertains.

SUMMARY OF THE INVENTION

The present inventors have made intensive researches to provide a novel therapeutic for preventing and treating bone diseases. As a result, we have found that IP-10 (interferon-γ-inducible protein 10) upregulates the expression of RANKL that plays an important role in the formation of osteoclasts and in turn the blockade of IP-10, in particular, by use of antibodies to IP-10, results in the inhibition of RANKL expression, being responsible for providing a novel therapeutic realm in bone diseases.

Accordingly, it is an object of this invention to provide a pharmaceutical composition for preventing or treating a disease or disorder associated with the expression of RANKL (receptor activator of NF-κB ligand).

It is another object of this invention to provide a method for inhibiting the expression of RANKL (receptor activator of NF-κB ligand).

It is still another object of this invention to provide a use of an antibody to IP-10 (interferon-γ-inducible protein 10) for manufacturing a medicament for preventing or treating a disease or disorder associated with the expression of RANKL.

It is further object of this invention to provide a method for screening an antibody drug candidate to inhibit the expression of RANKL.

It is still further object of this invention to provide a monoclonal antibody specially binding to IP-10.

Other objects and advantages of the present invention will become apparent from the detailed description to follow and together with the appended claims and drawings.

BRIEF DESCRIPTION OF THE DRAWINGS

The patent or application file contains at least one drawing executed in color (FIGS. 1, 2, 5, 7, and 8). Copies of this patent or patent application publication with color drawing(s) will be provided by the Office upon request and payment of the necessary fee.

FIGS. 9A-9C corresponds to the results of monoclonal antibodies produced hybridoma cell lines as deposited with the Korean Cell Line Research Foundation under Accession Nos. KCLRF-BP-00144, KCLRF-BP-00142 and KCLRF-BP-00143, respectively.

DETAILED DESCRIPTION OF THIS INVENTION

Figure 1:
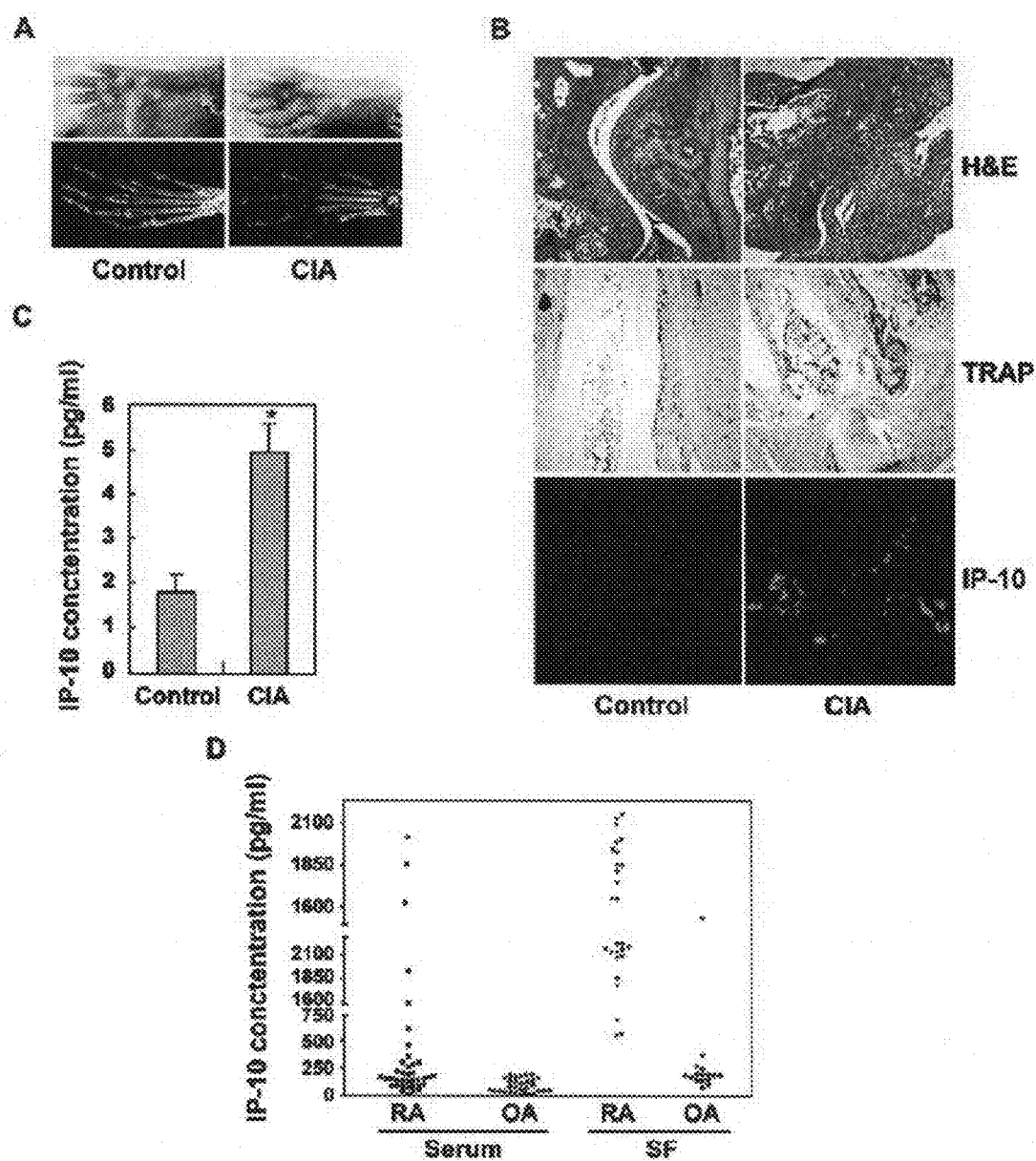
FIG. 1. Expression of IP-10 in collagen-induced arthritis (CIA). (A) Type II collagen was emulsified with CFA. DBA/1 mice were injected intradermally at the base of the tail with 150 μl of the emulsion on days 0 and 14, and the mice were killed on day 42. Paws were photographed by using a digital camera (top), and radiographs were taken with a soft X-ray machine (bottom). (B) Sections of the hind paws were stained with H&E (top), stained with TRAP (middle), or immunostained with antibody against IP-10 (bottom). (C) Concentrations of IP-10 in serum from control and CIA mice were measured by ELISA. Values were indicated as the mean±SD. *Significant difference between control and CIA (P<0.01). (D) Concentrations of IP-10 in serum and synovial fluids of patients with osteoarthritis (OA) or RA were analyzed as in (C).

In one aspect of this invention, there is provided a pharmaceutical composition for preventing or treating a disease or disorder associated with the expression of RANKL (receptor activator of NF-κB ligand), which comprises (a) a pharmaceutically effective amount of an antibody to IP-10 (interferon-γ-inducible protein 10); and (b) a pharmaceutically acceptable carrier.

In another aspect of this invention, there is provided a method for inhibiting the expression of RANKL (receptor activator of NF-κB ligand), which comprises administering to a subject a pharmaceutical composition comprising (a) a pharmaceutically effective amount of an antibody to IP-10 (interferon-γ-inducible protein 10); and (b) a pharmaceutically acceptable carrier.

In still another aspect of this invention, there is provided a use of an antibody to IP-10 (interferon-γ-inducible protein 10) for manufacturing a medicament for preventing or treating a disease or disorder associated with the expression of RANKL (receptor activator of NF-κB ligand).

The present inventors have made intensive researches to provide a novel therapeutic for preventing and treating bone diseases. As a result, we have found that IP-10 upregulates the expression of RANKL that plays an important role in the formation of osteoclasts and in turn the blockade of IP-10, in particular, by use of antibodies to IP-10, results in the inhibition of RANKL expression, being responsible for providing a novel therapeutic realm in bone diseases.

The present invention is directed to providing a novel therapeutic target relating to the etiology of bone diseases with bone destruction. More specifically, the present invention is drawn to providing the IP-10 protein as a novel therapeutic target relating to the etiology of bone diseases with bone destruction associated with RNAKL expression and osteoclast formation.

The present invention utilizes antibodies against IP-10 as active ingredients.

According to a preferred embodiment, the antibody to IP-10 inhibits the expression of RANKL and TNF-α (tumor necrosis factor-α), inter alia, in CD4+ T cells.

According to a preferred embodiment, the antibody to IP-10 inhibits the formation of osteoclasts.

The antibody against IP-10 contained in the pharmaceutical composition of the present invention includes any antibody specifically binding to IP-10. By "antibody" is meant an immunoglobulin protein which is capable of binding an antigen. Antibody as used herein is meant to include the entire antibody as well as any antibody fragments (e.g., F(ab')2, Fab', Fab, Fv and scFv) capable of binding the epitope, antigen or antigenic fragment of interest.

The antibodies used in this invention could be prepared according to conventional techniques such as a fusion method (Kohler and Milstein, *European Journal of Immunology*, 6:511-519(1976)), a recombinant DNA method (U.S. Pat. No. 4,816,56) or a phage antibody library (Clackson et al, *Nature*, 352:624-628(1991); and Marks et al, *J. Mol. Biol.*, 222:58, 1-597(1991)). The general procedures for antibody production are described in Harlow, E. and Lane, D., *Antibodies: A Laboratory Manual*, Cold Spring Harbor Press, New York, 1988; Zola, H., *Monoclonal Antibodies: A Manual of Techniques*, CRC Press, Inc., Boca Raton, Fla., 1984; and Coligan, CURRENT PROTOCOLS IN IMMUNOLOGY, Wiley/Greene, NY, 1991. The preparation of hybridoma cell lines for monoclonal antibody production is done by fusion of an immortal cell line and the antibody producing lymphocytes. This can be done by techniques well known in the art. Polyclonal antibodies may be prepared by injection of the antigen (IP-10 or its peptide sequence) to suitable animal, collecting antiserum containing antibodies from the animal, and isolating specific antibodies by any of the known affinity techniques.

According to a preferred embodiment, the antibody to IP-10 is a monoclonal antibody produced by a hybridoma cell line as deposited with the Korean Cell Line Research Foundation under Accession Nos. KCLRF-BP-00142, KCLRF-BP-00143, KCLRF-BP-00144 or KCLRF-BP-00145, more preferably, KCLRF-BP-00142 or KCLRF-BP-00144, most preferably, KCLRF-BP-00142.

The pharmaceutical composition of the present invention is useful in preventing or treating a disease or disorder associated with the expression of RANKL (receptor activator of NF-κB ligand). Preferably, the disease or disorder is a bone disease with bone destruction associated with the expression of RANKL, more preferably, osteoporosis, juvenile osteoporosis, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, metastatic bone diseases, periodontal bone loss, bone loss due to cancer and age-related loss of bone mass.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphates arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered via the routes used commonly and preferably, administered parenterally, i.e., by intravenous, intraperitoneal, intramuscular, subcutaneous, or local administration.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition, and physicians of ordinary skill in the art can determine an effective amount of the pharmaceutical composition for desired treatment. Generally, the pharmaceutical composition of the present invention may be administered with a daily dose of 0.0001-100 mg/kg (body weight). The term used herein "pharmaceutically effective amount" refers to an amount suitable to show and accomplish efficacies and activities of the anti-IP-10 antibodies of this invention.

According to the conventional techniques known to those skilled in the art, the pharmaceutical composition according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

In a further aspect of this invention, there is provided a method for screening an antibody drug candidate to inhibit the expression of RANKL (receptor activator of NF-κB ligand), which comprises the steps of:

(a) preparing an antibody specifically binding to IP-10 (interferon-y-inducible protein 10); and (b) analyzing the binding affinity of the antibody to IP-10, wherein the antibody having the binding affinity IP-10 is determined as the antibody drug candidate to inhibit the expression of RANKL.

The preparation of antibodies may be prepared according to conventional techniques described hereinabove. As antigens or immunogens, the IP-10 protein, its peptide fragments or peptide epitopes may be used.

The analysis for evaluating the binding affinity of antibodies to IP-10 may be conducted in accordance with immunoassay methods known to one skilled in the art. The immunoassay format includes, but not limited to, radioimmunoassay, radioimmuno-precipitation, enzyme-linked immunosorbent assay (ELISA), capture-ELISA, dot blot assay, Western blot assay, inhibition or competition assay and sandwich assay. The immunoassay procedures can be found in *Enzyme Immunoassay*, E. T. Maggio, ed., CRC Press, Boca Raton, Fla., 1980; Gaastra, W., Enzyme-linked immunosorbent assay (ELISA), in *Methods in Molecular Biology*, Vol. 1, Walker, J. M. ed., Humana Press, NJ, 1984; and Ed Harlow and David Lane, *Using Antibodies*, A Laboratory Manual, Cold Spring Harbor Laboratory Press, 1999.

For example, according to the radioimmunoassay method, the radioisotope (e.g., $P^{32}$ and $S^{35}$) labeled antibody or IP-10 may be used.

According to the ELISA method, the specific example of the present method may comprise the steps of: (i) coating a surface of a solid substrate with the IP-10 protein; (ii) incubating the IP-10 protein with antibodies to be analyzed as a primary antibody; (iii) incubating the resultant of step (ii) with a secondary antibody conjugated to an enzyme catalyzing colorimetric, fluorometric, luminescence or infra-red reactions; and (iv) measuring the activity of the enzyme.

The solid substrate coated with the primary antibody is hydrocarbon polymers such as polystyrene and polypropylene, glass, metals or gels. Most preferably, the solid substrate is a microtiter plate.

The enzyme catalyzing colorimetric, fluorometric, luminescence or infra-red reactions includes, but not limited to, alkaline phosphatase, β-galactosidase, Cytochrome $P_{450}$, and horseradish peroxidase. Where using alkaline phosphatase, bromochloroindolylphosphate (BCIP), nitro blue tetrazolium (NBT) and ECF (enhanced chemifluorescence) may be used as a substrate; in the case of using horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine, Pierce), TMB (3,3,5,5-tetramethyl-benzidine) and ABTS (2,2-Azine-di[3-ethylbenzthiazoline sulfonate]) may be used as a substrate.

Finally, the antibody having the binding affinity IP-10 is determined as the antibody drug candidate to inhibit the expression of RANKL.

According to a preferred embodiment, the antibody drug candidate is used for a drug for preventing or treating a bone disease with bone destruction associated with the expression of RANKL, more preferably, osteoporosis, juvenile osteoporosis, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, metastatic bone diseases, periodontal bone loss, bone loss due to cancer and age-related loss of bone mass.

In still further aspect of this invention, there is provided a monoclonal antibody specifically binding to IP 10 (interferon-γ-inducible protein 10), which is produced by a hybridoma cell line as deposited with the Korean Cell Line Research Foundation under Accession Nos. KCLRF-BP-00142, KCLRF-BP-00143, KCLRF-BP-00144 or KCLRF-BP-00145.

The following specific examples are intended to be illustrative of the invention and should not be construed as limiting the scope of the invention as defined by appended claims.

EXAMPLES

Materials and Methods

Reagents

Recombinant human RANKL, M-CSF, OPG, mouse IP-10, and antibody to IP-10 were obtained from PeproTech EC (London, UK). Antibodies against phospho-ERK, ERK, phospho-Akt, Akt, phospho-p38, and p38 were obtained from Cell Signaling Technology (Beverly, Mass.). Antibodies against NFATc1, NFATc2, and actin were obtained from San Cruz Biotechnology (Santa Cruz, Calif.). Antibodies against TNF-α and mouse IgG were from R&D Systems (Minneapolis, Minn.). Antibodies against CD4, IP-10 (R&D Systems), and F4/80 (eBioscience, San Diego, Calif.) were also used for immunohistochemistry experiments.

Mouse Strains and Human Samples

DBA/1 mice were purchased from Samtako (Osan, Korea) and were used for the induction of CIA. Other animal experiments used the ICR mouse strain. Mice were housed in specific-pathogen-free conditions, and all animal experiments were performed under a protocol approved by the institute committee of Seoul National University.

To measure IP-10 in serum and synovial fluids from RA patients, serum was obtained from 38 patients with RA and 31 patients with osteoarthritis under a protocol approved by the Institutional Review Board of Seoul National University Hospital. Synovial fluid was obtained from 28 RA and 16 osteoarthritis patients, respectively.

Induction and Assessment of CIA

Type II collagen (Chondrex, Seattle, Wash.) was dissolved in 50 mM acetic acid at 4° C. (2 mg/ml) and was emulsified with an equal volume of CFA (Chondrex) containing 2 mg/ml *Mycobacterium tuberculosis*. DBA/1 mice were injected intradermally at the base of the tail with 150 μl of the emulsion. After 14 day, type II collagen (CII) was emulsified with IFA and injected as described above. The severity of arthritis was assessed with a paw swelling score as follows: 0=normal, 1=swelling of toes, 2=swelling of sole or increased swelling, 3=severe swelling or swelling of entire paw. On day 42, a radiograph was taken with a soft X-ray or a microcomputed tomography apparatus. Paws were fixed, decalcified, and sectioned. Serum was obtained for ELISA.

Treatment with Antibody to IP-10

After the first immunization with CII (day 14), mice were boosted with CII and further injected i.v. in the tail vein with control IgG or anti-IP-10 antibody (200 μg/mouse). On day 42, paws and serum were collected for histology and ELISA, respectively.

Histology and Immunostaining

Tissues were removed and fixed in 4% paraformaldehyde (Sigma) for 1 day at 4° C. and were then decalcified in 12% EDTA. Decalcified bones were paraffin-embedded and sectioned. Sections were stained with H&E and TRAR For immunostaining experiments, sections were dewaxed with xylene and then dehydrated with ethanol. After nonspecific binding was blocked with 2% BSA, sections were incubated for 1 h with the primary antibodies in PBS containing 2% BSA. Sections were washed three times with PBS and then incubated with the appropriate secondary antibodies (1:5000). After washing three times, the sections were examined under a confocal microscope.

Isolation of Osteoclast Precursors and Activated CD4$^+$ T Cells

Osteoclast precursors and mature osteoclasts were prepared as described previously.[25] Briefly, bone marrow cells were obtained from long bones, suspended in α-MEM (Welgene, Korea) containing 10% FBS and antibiotics in the presence of M-CSF (10 ng/ml), and cultured for 1 day. After 1 day, nonadherent cells were cultured for 3 days in the presence of M-CSF (30 ng/ml), and adherent cells were used as osteoclast precursors. Mature osteoclasts were generated by cocultures of bone marrow cells and calvarial osteoblasts. CD4$^+$ T cells were isolated from mouse spleens. Spleens were mashed in HBSS containing 3× antibiotics. Cells were harvested, and RBCs were removed with RBC lysis buffer (Sigma). The remaining cells were collected and separated by using a Ficoll-Histopaque discontinuous gradient. The interface containing the cells was washed with PBS, resuspended in RPMI (Gibco BRL) containing 10% FBS and antibiotics, and then cultured for 1 day. Nonadherent cells were cultured for 4 day in the presence of IL-2 (50 ng/ml). Activated CD4$^+$ and CD8$^+$ T cells were purified by positive selection by using anti-CD4 or anti-CD8 magnetic beads, respectively. The purity of CD4$^+$ and CD8$^+$ T cells was ≧95% as assessed by flow cytometry (FACSCalibur, BD Biosciences).

Western Blotting

Cells were lysed in lysis buffer (50 mM Tris-Cl, 150 mM NaCl, 5 mM EDTA, 1% Triton X-100, 1 mM NaF, 1 mM Na3VO4, and 1% sodium deoxycholate) containing protease inhibitors. Cell lysates were centrifuged at 13,000 rpm, and equal amounts of protein were electrophoresed on 10-15% SDS-PAGE gels, transferred to polyvinylidene difluoride membranes, and subjected to Western blotting with antibodies to IP-10, NFATc1, NFATc2, phospho-ERK, ERK, phospho-Akt, Akt, phospho-p38, p38, and actin. Signal was visualized by using enhanced chemiluminescent reagents.

RT-PCR Analysis

For RT-PCR assays, total RNA was isolated by using TRIzol reagent (Invitrogen, Carlsbad, Calif.) as recommended by the manufacturer. Two micrograms of total RNA from each sample was reverse transcribed with Superscript II reverse transcriptase (Invitrogen), and 1 μl of cDNA was used as a template for PCR. The primers used were as follows: RANKL sense, 5'-CAGGTTTGCAGGACTCGAC-3' (SEQ ID NO: 1); RANKL antisense, 5'-AGCAGGGAAGGGTTGGACA-3' (SEQ ID NO: 2); TNF-α sense, 5'-ACACCGTCAGC-CGATTTGC-3' (SEQ ID NO: 3); TNF-α antisense, 5'-CCCTGAGCCATAATCCCCTTT-3' (SEQ ID NO: 4); IFN-γ sense, 5'-GTTTGAGGTCAACAACCCAC-3' (SEQ ID NO: 5); IFN-γ antisense, 5'-AATCTGAGTTCAGT-CAGCCG-3' (SEQ ID NO: 6); CXCR3 sense, 5'-GCCAC-CCATTGCCAGTACAAC-3' (SEQ ID NO: 7); CXCR3 antisense, 5'-TCCCACAAAGGCATAGAGCAGC-3' (SEQ ID NO: 8); IP-10 sense, 5'-AAGCCTCCCCATCAGCACCA-3' (SEQ ID NO: 9); IP-10 antisense, 5'-TGTCCATCCATCG-CAGCACC-3' (SEQ ID NO: 10); GAPDH sense, 5'-CAAG-GCTGTGGGCAAGGTCA-3' (SEQ ID NO: 11);" GAPDH antisense 5'-AGGTGGAAGAGTGGGAGTTGCTG-3' (SEQ ID NO: 12). The amplified PCR products were separated on a 1% agarose gel. Densitometric values for each band were quantified by using the Image Pro-plus program version 4.0 (Media Cybernetics).

ELISA

Concentrations of cytokines in serum, synovial fluids, and culture medium were measured with sandwich ELISA kits (R&D Systems, Minneapolis) according to the manufacturer's instructions. Briefly, 50 μl of serum, synovial fluid, or culture medium was added to each well, which had been previously coated with antibodies to IP-10, RANKL, TNF-α, or IFN-γ. After a 2-hr incubation, wells were washed three times with wash buffer and then incubated with enzyme-linked antibodies to IP-10, RANKL, TNF-α, or IFN-γ. After the plate was washed five times with wash buffer, a substrate solution was added to each well. After 30 min, the color reaction was stopped by the addition of stopping solution, and the OD was read on a microtiter ELISA plate reader at an absorbance of 450 nm.

Osteoclastogenesis

Osteoclast precursors and CD4$^+$ cells were cocultured in 48-well plates for 6 days in the presence of M-CSF (10 ng/ml) and IP-10 (100 to 200 ng/ml). Cells were fixed with 3.7% formalin, permeabilized in 0.1% Triton X-100, and stained by the addition of TRAP solution (Sigma).

Migration Assay

The migration of CD4$^+$ T cells and osteoclast precursors was evaluated by using a Boyden chamber (24-well, 3- or 8-μm pore size membrane; Corning Costar, Cambridge, Mass.) as previously described.[26] Briefly, osteoclast precursors were first treated for 3 days with M-CSF. Osteoclast precursors or CD4$^+$ T cells were then loaded in the upper well, and the lower well was loaded with α-MEM or RPMI, respectively, in the presence or absence of mouse IP-10 (100 ng/ml). After incubation for 6 to 10 hr, the migrated cells were counted.

Alternatively, the migration of CD4$^+$ T cells was evaluated using the anti-IP-10-antibodies of the present invention loaded with the upper well.

Preparation of Retrovirus

Retrovirus was prepared by using Plat E packaging cells. pMX-IRES-EGFP vectors were kindly provided by Dr. Nacksung Kim (University of Chonnam). The coding sequence for IP-10 was cloned by PCR by using a pair of primers for the mouse IP-10 gene and was inserted into pMX-IRES-EGFP vector. Plat E cells were plated in 10-cm dishes and were transiently transfected with pMX-IRES-EGFP or pMX-IP-10-IRES-EGFP DNA by using Lipofectamine2000 as recommended by the manufacturer. Forty-eight hours after transfection, the culture medium was collected and used as a retrovirus.

Administration of IP-10 into Cells and Mice

Osteoclast precursors were infected with control or IP-10 retrovirus in the presence of M-CSF (30 ng/ml) and polybrene (6 μg/ml) for 8 hr. The medium was replaced with fresh α-MEM containing FBS, antibiotics, and M-CSF (30 ng/ml)

and was further incubated for 2 days. GFP-expressing cells were observed by confocal microscopy. For in vivo study, control or IP-10 retrovirus (50 μl) administration was performed by injection into the tibial metaphysis of ICR mice. Control or IP-10 retrovirus was injected weekly for 6 wk.

Preparation of Monoclonal Antibodies Against IP-10

Immunization of Mice

IP-10 contained in complete Freud's adjuvant (Qiagen, Calif.) was used for immunizing eight-week old BALB/c mice by intraperitoneal injection. After 2 weeks, the mice were immunized in the same manner as described above and again immunized via tail vein using IP-10 (half dose of initial immunization) contained PBS. Two days later, serum was collected from tail and used for ELISA for determining amount of antibodies induced.

Preparation of Myeloma Cells

Myeloma cells (Sp2/O-/Ag14) were taken out of liquid nitrogen tanks two weeks prior to cell fusion, and cultured in complete DMEM. The density of cell culture was adjusted to $2 \times 10^5$ cells/ml one day before performing cell fusion.

Preparation of Mouse Feeder Cell

Healthy mice were sacrificed by cervical dislocation and their peritoneum was exposed by skin removal. Eight ml of 0.34 M cold sucrose solution was injected into peritoneum using 10-ml syringe with 10-G needle. Then, the sucrose solution containing cells was collected, transferred into a cold 50-ml conical tube and mixed with 20 ml of cold HAT. The cell solution was centrifuged at 100×g for 5 min and cell pellet formed was resuspended in 35 ml of cold HAT. Aliquots ($1 \times 10^5$ cells) of the cell suspension were plated into each well of 96-well plates and cultured in $CO_2$ incubator.

Preparation of Splenocytes

Spleen was obtained from immunized mice to obtain primary splenocytes. Splenocytes were passed through a wire 60-mesh and red blood cells were removed by incubating with 10 mM HEPES (pH 7.2) containing 0.830% $NH_4Cl$.

Cell Fusion

Primary splenocytes obtained thus were fused with the mouse myeloma cell line in the presence of polyethylene glycol (PEG; molecular wt. 1300-1600; Sigma). The resultant was plated into 96-well plates containing HAT and cultured to a confluency of 10-50%. Hybridoma cells were screened by ELISA and antibody-producing cells were subjected to subsequent rounds of subcloning, by limiting dilution, to obtain stable hybridomas.

Production of Ascites Fluids

Eight-week old BALB/c mice were intraperitoneally administered with 0.5-1 ml of pristine. Following one week of administration, $5 \times 10^6 - 1 \times 10^7$ hybridomas were intraperitoneally injected into mice. One week later, ascites fluids were collected using a syringe with 18-G needle and centrifuged at 1,500×g for 10 min. The supernatants were transferred into tubes and stored at −20° C. Finally, we obtained five monoclonal antibodies (#124, #31, #28, #137 and #43).

Western Blotting for Confirming the Production of Monoclonal Anti-IP-10 Antibodies Western blotting assay was carried out in the same manner as described above, except for antigen (purified IP-10) and primary antibody. As results, it was revealed that among five monoclonal antibodies to IP-10, four antibodies (#124, #31, #28 and #137) were positive to IP-10 antigen. Of them, the antibody numbered #28 showed the highest positive-signal to IP-10 and the other antibodies similarly showed low signal intensities. Four hybridoma cell lines producing antibodies to IP-10 were denoted as "#124-11-2", #31-6-1", "28-2-3" and #137-2-1", respectively, which were deposited on Aug. 30, 2006 in the International Depository Authority, the Korean Cell Line Research Foundation and were given accession numbers KCLRF-BP-00142, KCLRF-BP-00143, KCLRF-BP-00144 and KCLRF-BP-00145, respectively.

Statistical Analysis

Each experiment was performed in triplicate and was repeated at least twice, and all quantitative data are presented as means±SDs. Statistical differences were analyzed by Student's t test.

Results

Expression of IP-10 in Inflamed Joints in CIA and RA

To investigate whether IP-10 is expressed in the synovium in CIA, DBA/1 mice were immunized intradermally with an emulsion of bovine collagen type II (CII) and CFA at the base of the tail on day 0 and boosted with a CII emulsion on day 14. Swelling of the digits is first observed on day 20, and the mice were killed on day 42. Histologic analysis of the paws showed that the inflamed joints of mice with CIA were massively infiltrated with mononuclear cells, and cartilage destruction and bone erosion of the joint were greater in CIA mice than in control mice (FIGS. 1,A and B). IP-10 was slightly expressed in the control mice but was greatly increased in the inflamed joints of CIA mice (FIG. 1B). Also, IP-10 expression in serum was significantly higher in CIA mice than in control mice (FIG. 1C). As shown in FIG. 1D, IP-10 concentrations were greatly increased in serum and synovial fluids from RA patients compared with osteoarthritis patients. These results suggest that IP-10 is significantly elevated in the synovium in RA and likely contributes to CIA progression.

Neutralizing Anti-IP-10 Antibody Suppresses the Progression of CLA

Figure 2:
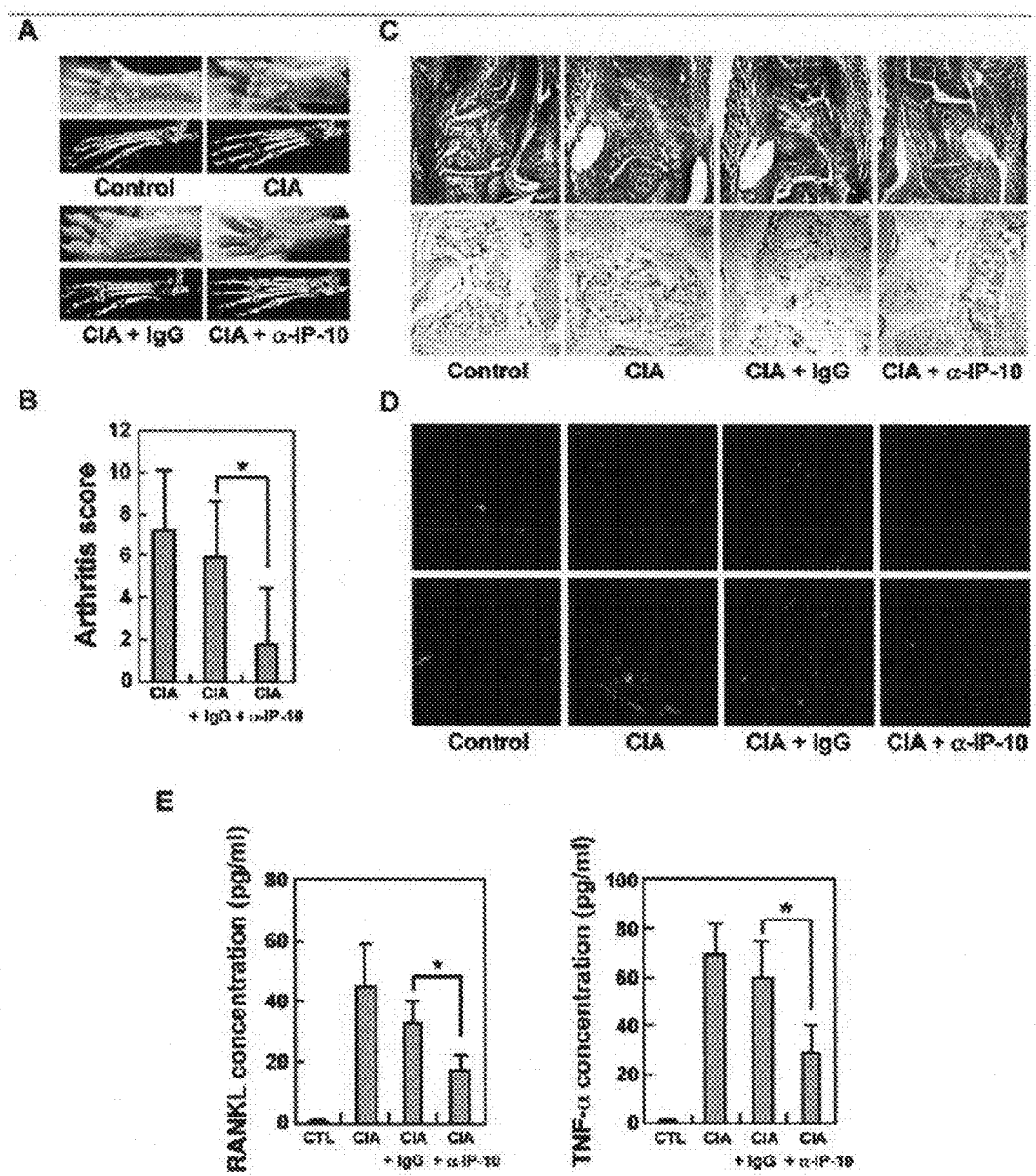
FIG. 2. Neutralizing anti-IP-10 antibody treatment ameliorates CIA progression. (A) At 14 day after the first immunization, the mice were boosted with emulsion of CII and further injected i.v. with equal volumes of control IgG (200 µg/mouse) and anti-IP-10 antibody (200 µg/mouse). At the end of the arthritis (day 42), the paws were photographed using a digital camera (top) and three-dimensional image of paws were taken with a µ-CT apparatus (bottom). (B) The severity of arthritis was assessed by assigning a score of 0-3 based on the degree of swelling for each paw as described under "Materials and Methods." Each value was indicated as the mean±SD. *Significant difference between the indicated groups (P<0.05). (C) Sections of the paws were stained with H&E (top) and TRAP (bottom). (D) Sections of the paws were immunostained with antibody for CD4 (top) and F4/80 (bottom) as described in "Materials and methods." (E) The serum of control, CIA, CIA plus IgG, and CIA plus α-IP-10 antibody mice were analyzed for RANKL and TNF-α by ELISA. Values were indicated as the mean±SD. *Significant difference between the indicated groups (P<0.05).

To investigate the role of IP-10 during the progression of CIA, we injected DBA/1 mice intradermally with the CII emulsion, injected a CII booster on day 14, and then intravenously injected equal volumes of control IgG (200 μg/mouse; n=5) and anti-IP-10 antibody (200 μg/mouse; n=5). After a 4 weeks period without treatment, paw swelling in the mice injected with anti-IP-10 antibody was significantly reduced in mice injected with control IgG-injected mice (FIGS. 2,A and B). Microcomputed tomography analysis showed that bone erosion was much less in the mice injected with anti-IP-10 antibody than in the control IgG-injected mice (FIG. 2B). Hematoxylin-eosin (H&E) and tartrate-resistant acid phosphatase (TRAP) staining showed that the anti-IP-10 antibody significantly attenuated both bone loss and the number of osteoclasts in the CIA mice (FIG. 2C). Importantly, CD4$^+$ T cells and F4/80$^+$ macrophages infiltrated into the synovium of CIA and IgG-injected CIA mice, but anti-IP-10 antibodies inhibited the infiltration of CD4$^+$ T cells and F4/80$^+$ macrophages (FIG. 2D). Furthermore, serum concentrations of RANKL and TNF-α were significantly lower in CIA mice injected with anti-IP-10 than in CIA or IgG-injected CIA mice (FIG. 2 E). These results suggest that the induction of IP-10 in the synovium of inflamed joints is important for the progression of RA.

RANKL Induces IP-10 Expression by Osteoclast Precursors

Figure 3:
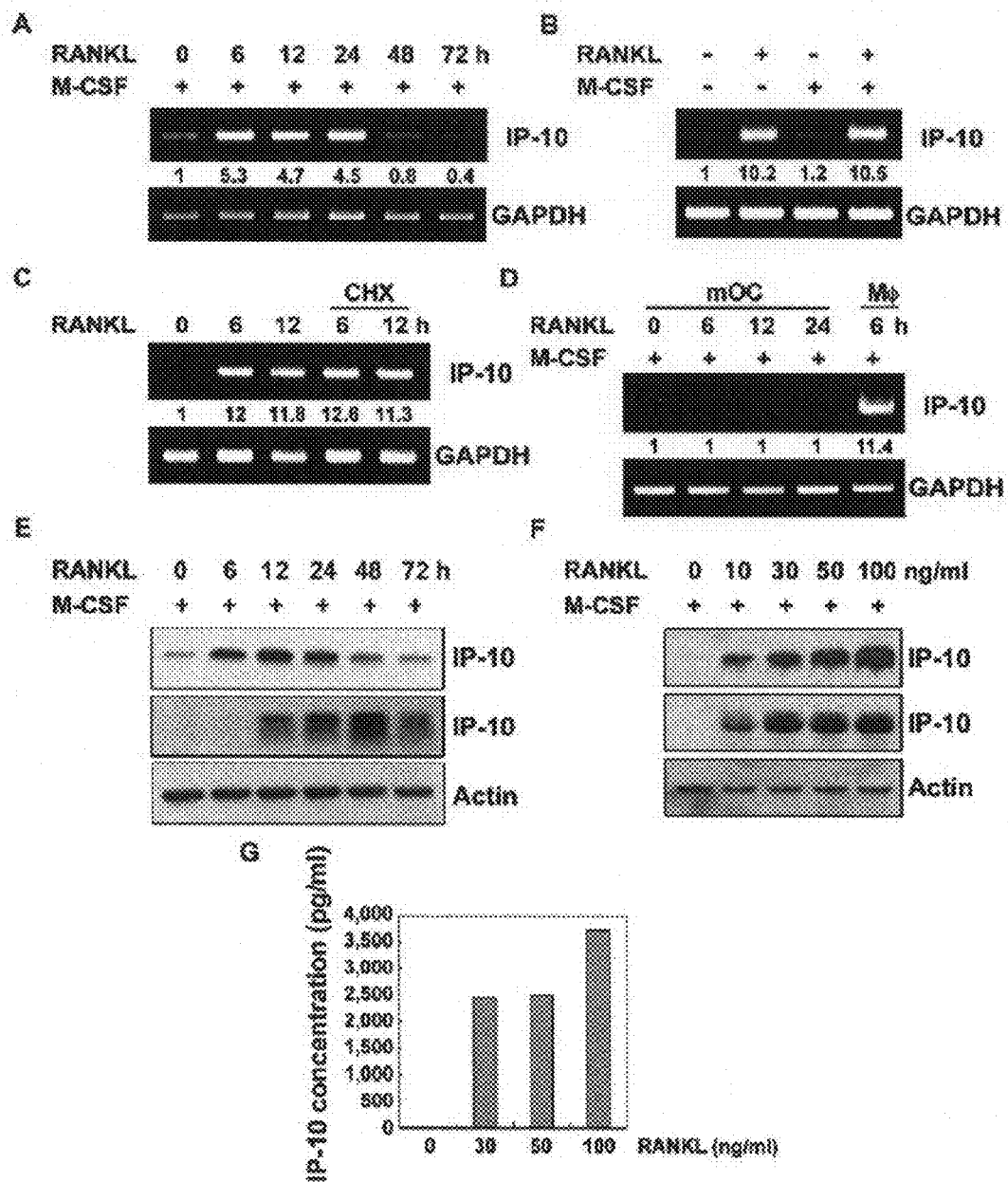
FIG. 3. RANKL induces IP-10 expression in osteoclast precursors. (A) Osteoclast precursors were stimulated with RANKL (100 ng/ml) in the presence of M-CSF (30 ng/ml) for the indicated time. The mRNA expression levels of the indicated genes were analyzed by RT-PCR. Densitometric values for each band were quantified by densitometric analysis and were normalized to the GAPDH intensity. (B) Osteoclast precursors were stimulated with M-CSF (30 ng/ml), RANKL (100 ng/ml), or both for 6 h. (C) Osteoclast precursors were pretreated with or without cyclohexamide (CHX; 3 µg/ml) for 30 min and further stimulated with RANKL (100 ng/ml) for the indicated time. (D) Mature osteoclasts (mOC) were isolated, and mature osteoclasts and osteoclast precursors (Mϕ) were stimulated with RANKL (100 ng/ml) for the indicated time. (E) Osteoclast precursors were stimulated as in (A). After stimulation, cell lysates (top) or culture media (middle) were analyzed by Western blotting with antibodies for IP-10. The same membrane was stripped and reprobed with antibody to actin. (F) Osteoclast precursors were stimulated with different concentrations of RANKL. After incubation for 24 h, cell lysates (top) or culture media (middle) were analyzed by Western blotting as in (E). (G) Osteoclast precursors were stimulated as in (F). The culture media were collected from the stimulated cells. Concentrations of IP-10 in the culture medium were measured by ELISA.

The expression of IP-10 in inflamed joints results in severe arthritis and infiltration of CD4$^+$ T cells and F4/80$^+$ macrophages, which raises the question of how IP-10 is increased in inflamed joints. Previously, we found that RANKL significantly induces MIG expression in osteoclast precursors.[26] MIG is a CXC chemokine that shows similarity with IP-10. Therefore, to determine whether RANKL mediates IP-10 expression in osteoclast precursors, cells were stimulated with RANKL (100 ng/ml) for various times. RT-PCR analysis showed that the expression of IP-10 increased from 6 h to 24 h in response to RANKL (FIG. 3A). Macrophage colony-stimulating factor (M-CSF) alone did not induce IP-10 expression and had no synergistic effect on IP-10 expression in response to RANKL (FIG. 3B). Furthermore, RANKL directly induced IP-10 expression in osteoclast precursors without new protein synthesis but did not induce IP-10 expression in mature osteoclasts (FIGS. 3,C and D). To confirm this result, levels of IP-10 protein in osteoclast precursors were measured by Western blotting. Consistent with the results of the RT-PCR analyses, RANKL induced the expression of IP-10 protein in a time-dependent manner, and expression declined after 48 h (FIG. 3E). By 24 h after RANKL treatment, protein levels of IP-10 increased in a dose-dependent manner (FIG. 3F). To determine the amount of secreted IP-10, the level of IP-10 in the culture medium was assayed by ELISA, and these results were consistent with the Western blot analysis (FIG. 3G). These results suggest that RANKL mediates the induction of IP-10 in osteoclast precursors.

Figure 6:
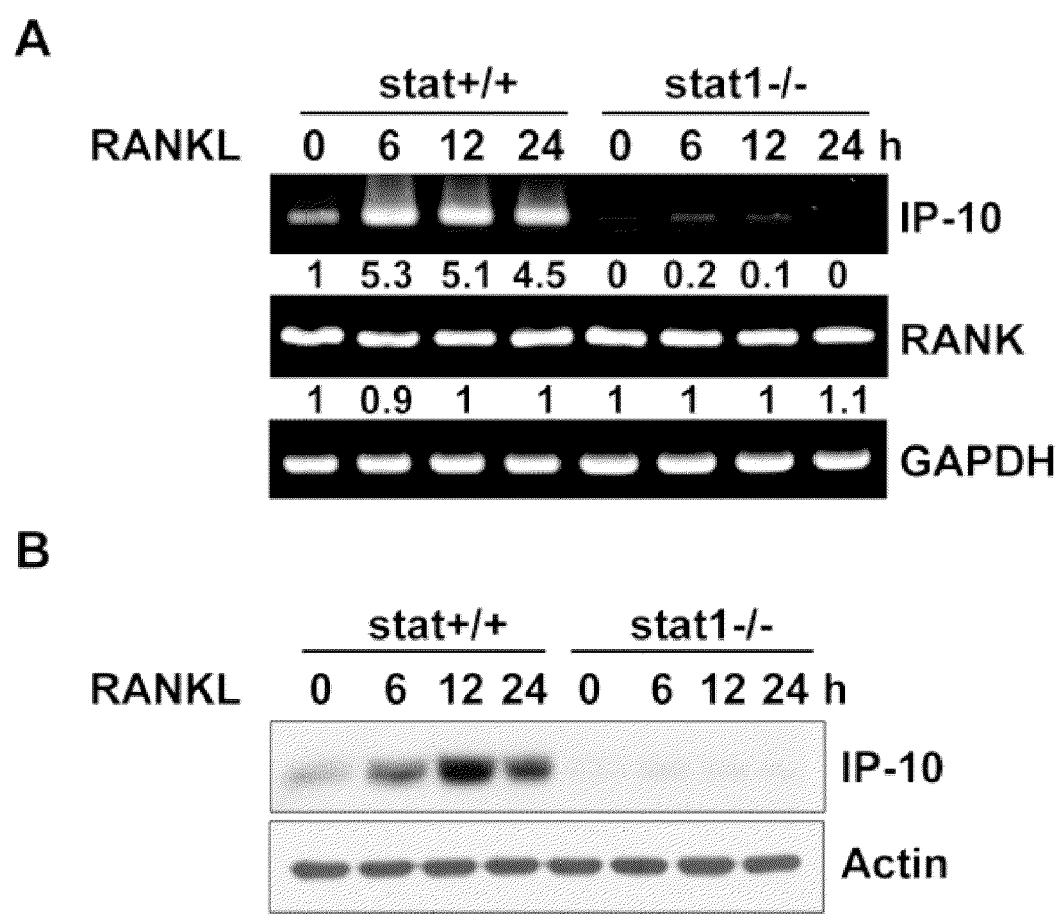
FIGS. 6A-6B. RANKL induces IP-10 through a STAT1-dependent pathway. (A) Osteoclast precursors were obtained from wild-type and STAT1-deficient mice, and both cells were stimulated with RANKL (100 ng/ml) for the indicated time. The mRNA expression levels of the indicated genes were analyzed by RT-PCR. Densitometric values for each band were quantified by densitometric analysis and were normalized to the GAPDH intensity. (B) Osteoclast precursors were stimulated as in (A). IP-10 expression was analyzed by Western blotting with an antibody to IP-10. The same membrane was stripped and reprobed with antibody to actin.

Because stat1 is thought to be an important transcription factor in IP-10 expression,[13] we investigated whether stat1 is required for IP-10 expression in response to RANKL. RANKL induces IP-10 expression in wild-type osteoclast precursors, but this induction was reduced in stat1-deficient osteoclast precursors (FIG. 6). These results suggest that RANKL promotes IP-10 expression through the stat1 pathway in osteoclast precursors.

IP-10 Up-Regulates Osteoclastogenic Cytokine Expression in $CD4^+$ T Cells

To examine the hypothesis that the IP-10 expressed by osteoclast precursors plays a critical role in activation of T cells in the synovium of inflamed joints, we first investigated whether IP-10 induces the expression of nuclear factor of activated T cells (NFAT), because the induction of NFAT is essential for T cell activation. Western blot analysis showed that IP-10 induces the expression of NFATc1 and NFATc2 and stimulates the phosphorylation of ERK, Akt, and p38 MAPK in $CD4^+$ T cells (FIG. 4A). Also, IP-10 induces the expression of NFATc1 and NFATc2 and stimulates the phosphorylation of ERK, Akt, and p38 MAPK in $CD8^+$ T cells, but to a lower extent (data not shown).

Because it has been reported that activated T cells express RANKL and mediate osteoclastogenesis,[27] we examined whether IP-10 induces the expression of RANKL or osteoclastogenic cytokines in $CD4^+$ T cells. As shown in FIG. 4B, IP-10 significantly induced RANKL and TNF-α, but the basal level of IFN-γ gradually decreased. Cyclohexamide had no effect on the induction of RANKL or TNF-α by IP-10 (FIG. 4C). To confirm this result, the amount of secreted RANKL, TNF-α, and IFN-γ in the culture medium was measured by ELISA, and these results were consistent with the RT-PCR analyses (FIG. 4D). In contrast with the result in $CD4^+$ T cells, IP-10 did not induce RANKL or TNF-α expression in $CD8^+$ T cells (FIG. 4E).

CXCR3, the receptor for IP-10, is functionally expressed on activated T cells and also binds to the other ligands MIG and I-TAC.[28] Previously, we found that RANKL enhances MIG expression in osteoclast precursors.[26] Therefore, to determine whether the expression of RANKL or TNF-α in $CD4^+$ T cells is induced by MIG, $CD4^+$ T cells were stimulated with MIG for various times. RT-PCR analysis showed that MIG did not induce RANKL or TNF-α in $CD4^+$ T cells (FIG. 4F). These results suggest that IP-10 can activate $CD4^+$ T cells and specifically induces the expression of RANKL and TNF-α in $CD4^+$ T cells.

IP-10 Enhances Osteoclast Differentiation in Cocultures of $CD4^+$ Cells and Osteoclast Precursors To examine the potential of IP-10 in osteoclastogenesis, osteoclast precursors were cocultured with $CD4^+$ T cells in the presence of IP-10. IP-10 induced TRAP-positive osteoclasts in a dose-dependent manner (activated $CD4^+$ T cells were cocultured with osteoclast precursors in the presence of the indicated concentrations of IP-10 and M-CSF (10 ng/ml) for 6 days. Cells were fixed and then stained with TRAP. TRAP-positive cells were counted as osteoclasts. Asterisks indicate columns significantly different (P<0.01) from control. However, IP-10 did not mediate osteoclast differentiation by coculturing osteoclast precursors and $CD8^+$ T cells (data not shown). Osteoclast differentiation induced by IP-10 was suppressed in the presence of osteoprotegerin (OPG) (activated $CD4^+$ T cells and osteoclast precursors were cocultured for 6 days with IP-10 (200 ng/ml) or IP-10 plus OPG (500 ng/ml) in the presence of M-CSF (10 ng/ml). *Significant difference between the indicated groups (P<0.01). These results suggest that IP-10 induces osteoclast differentiation by inducing RANKL expression in $CD4^+$ T cells.

TNF-α can also induce osteoclast differentiation in the absence of RANKL and has a synergistic effect on osteoclast differentiation in the presence of RANKL.[29,30] We further examined the effect of TNF-α in osteoclast differentiation by coculture of osteoclast precursors and $CD4^+$ T cells in the presence of IP-10. Osteoclast differentiation regulated by IP-10 was suppressed in the presence of antibody to TNF-α compared with control IgG (activated $CD4^+$ T cells and osteoclast precursors were cocultured for 6 days with control IgG (2 µg/ml) or antibody to TNF-α (2 µg/ml) in the presence of IP-10 (200 ng/ml) and M-CSF (10 ng/ml). *Significant difference between the indicated groups (P<0.05). These results suggest that IP-10 stimulates osteoclast differentiation in cocultures of $CD4^+$ T cells and osteoclast precursors through expression of both RANKL and TNF-α.

Figure 7:
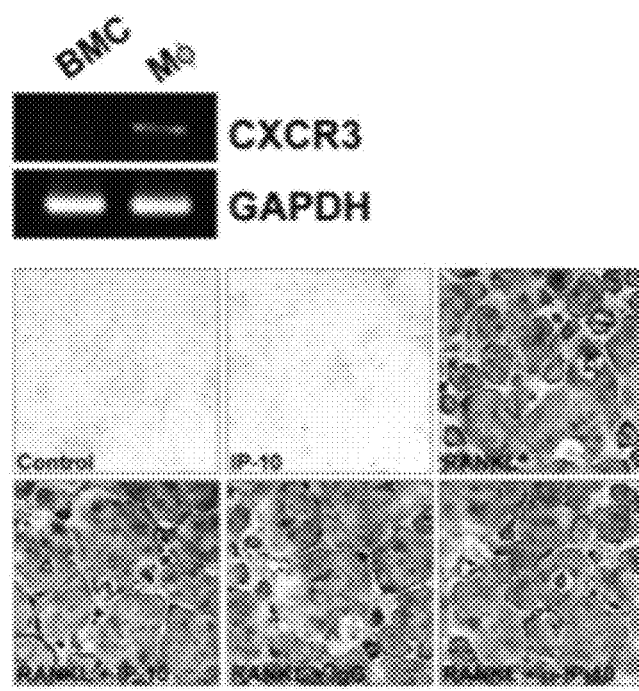
FIGS. 7A-7B. IP-10 does not induce differentiation of osteoclast precursors. (A) Bone marrow cells (BMC) and osteoclast precursors (Mϕ) were obtained, and RT-PCR was carried out for the indicated genes (top). Osteoclast precursors were cultured in 48-well plates for 6 d with IP-10 (100 ng/ml), RANLK (50 ng/ml), IP-10 plus RANKL, RANKL plus control IgG (2 µg/ml), or RANKL plus antibody to IP-10 (2 µg/ml) in the presence of M-CSF (30 ng/ml). Cells were fixed and stained with TRAP (bottom). (B) TRAP-positive cells were counted as osteoclasts.
Figure 7:
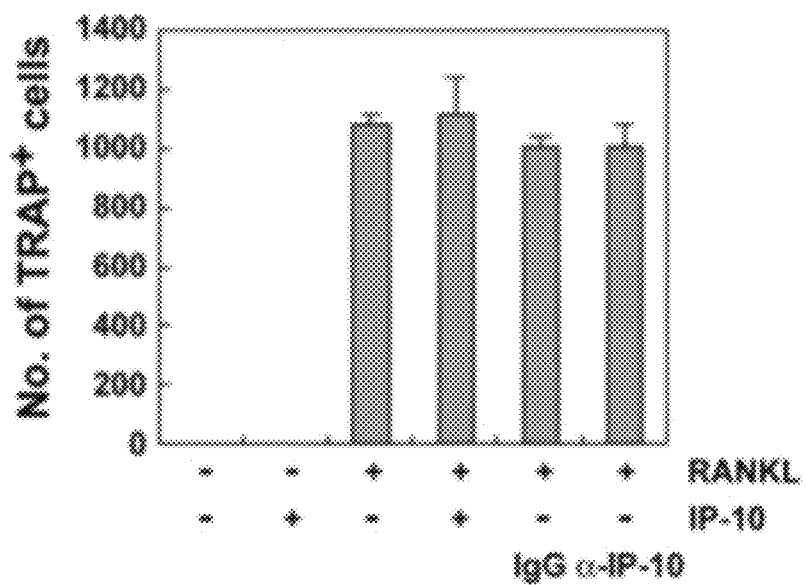

We showed previously that the expression of CXCR3 increases in osteoclast precursors with M-CSF treatment.[26] Thus, to determine whether IP-10 directly induces osteoclast differentiation from osteoclast precursors, osteoclast precursors were cultured with IP-10 for 6 d in the presence of M-CSF or M-CSF plus RANKL. Also, osteoclast precursors were cultured for 6 d with M-CSF plus RANKL in the presence of neutralizing antibody to IP-10 or control IgG. IP-10 did not induce the differentiation of osteoclast precursors and had no synergistic effect on osteoclast differentiation by RANKL (FIG. 7).

IP-10 Promotes Bone Erosion Through Recruitment of CD4 and Macrophages

To examine whether IP-10 can induce the infiltration of inflammatory cells, such as $F4/80^+$ macrophages and $CD4^+$ T cells, and causes bone erosion in vivo, we used a retrovirus for IP-10 administration to mice. Osteoclast precursors were infected with culture supernatants containing control or IP-10 retroviruses. Retrovirus-infected cells were determined by confocal microscopy, and the infection efficiency of both retroviruses was more than 90%. IP-10 protein was greatly increased in IP-10 retrovirus-infected cells (FIG. 5A). Next, control and IP-10 retrovirus were locally injected into the tibial metaphysis of mice, 6 times for 6 wk. IP-10 expression was observed at the injected sites (data not shown). Bone erosion was greatly increased in IP-10-injected mice (FIG. 5B). In addition, histologic analysis showed that bone erosion was greater in IP-10-injected mice than in control-injected mice. IP-10 significantly enhanced osteoclast formation compared with that in control mice (FIG. 5C).

Figure 8:
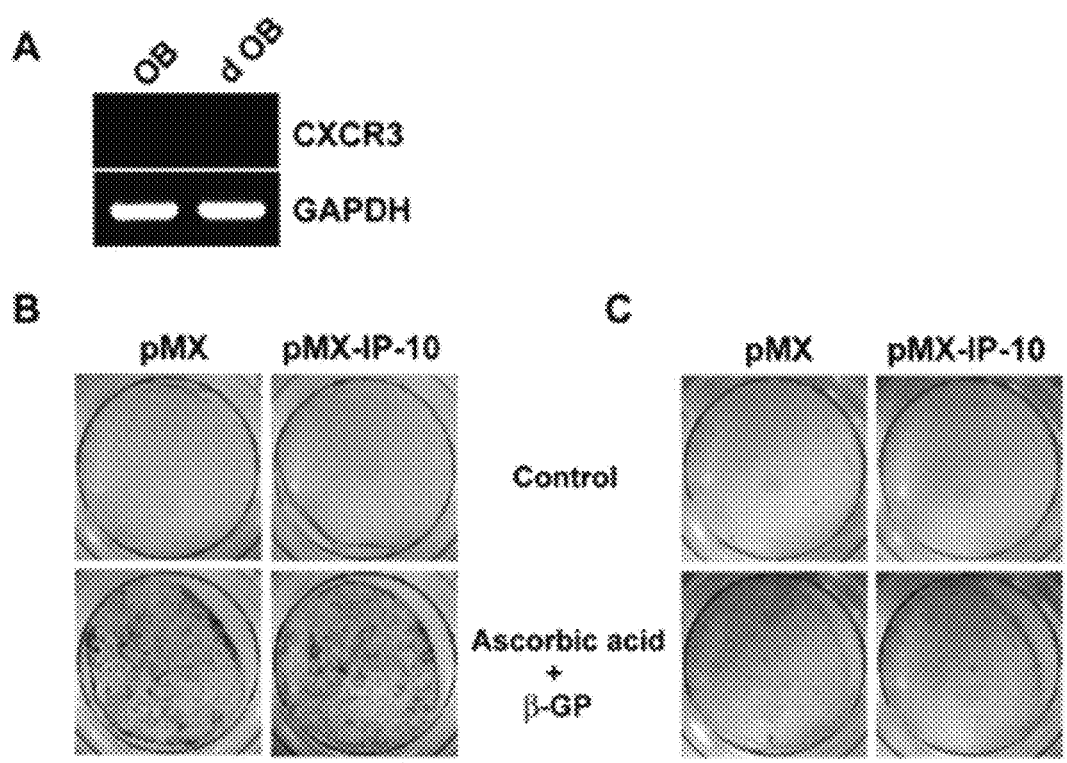
FIGS. 8A-8C. IP-10 has no effect on calvarial osteoblast differentiation and bone formation. (A) Calvarial osteoblasts were treated for 7 days with ascorbic acid (50 µg/ml) and β-glycerophosphate (5 mM) to generate differentiated osteoblasts. Osteoblasts precursors (OB) and differentiated osteoblasts (d OB) were obtained, and RT-PCR was carried out for CXCR3 (35 cycles) and GAPDH (23 cycles). (B and C) Calvarial osteoblasts were infected with control or IP-10 retroviruses for 48 h in the presence of polybrene (6 µg/ml). Cells were cultured with or without ascorbic acid (50 µg/ml) and β-glycerophosphate (β-GP; 5 mM) for 7 d (alkaline phosphatase staining, B) or for 15 d (Alizarin red staining, C).

We next analyzed the effect of IP-10 on osteoblast differentiation and bone formation in cultures of calvarial osteoblasts, because bone mass were greatly decreased in the IP-10-injected mice. We did not detect expression of CXCR3 in calvarial osteoblasts or differentiated osteoblasts. In addition, calvarial osteoblasts were infected with control or IP-10 retroviruses and cultured for 2 d, and cells were treated with ascorbic acid and β-glycerophosphate for 7 or 15 d and stained by alkaline phosphatase or alizarin red, respectively. IP-10 did not affect osteoblast differentiation or bone formation (FIG. 8). These results show that IP-10-induced bone erosion is mediated by increasing osteoclast formation.

IP-10 is known to play a critical role in the recruitment of T cells. To determine whether IP-10 induces the recruitment of inflammatory cells into bone in vivo, tissue sections were immunostained with antibodies against CD4 and F4/80. The infiltration of $CD4^+$ T cells and $F4/80^+$ macrophages was increased in the tissues injected with IP-10 retrovirus (FIG. 5D). Furthermore, IP-10 induced the migration of $CD4^+$ T cells and $F4/80^+$ macrophages in vitro (FIG. 5E). Integrin CD11a and CD18 were increased in response to IP-10 in $CD4^+$ T cells (data not shown). These results show that IP-10 mediates bone erosion through osteoclast formation, which is associated with recruitment of $CD4^+$ T cells and $F4/80^+$ macrophages.

Figure 9A:
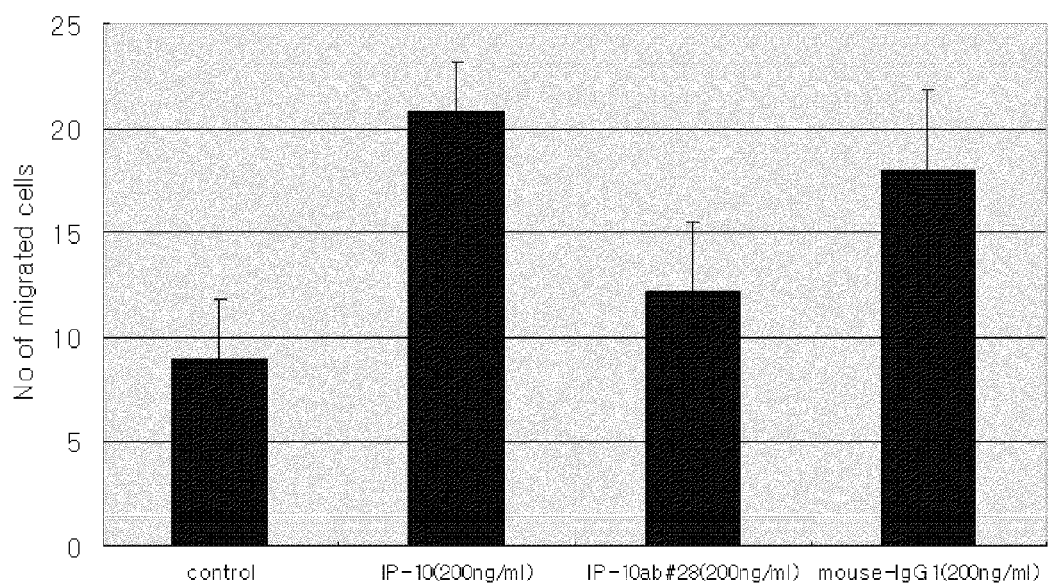
FIGS. 9A-9C. Anti-IP-10 antibodies of the present invention inhibit the migration of CD4+ T cells. The migration of CD4+ T cells in response to IP-10 was analyzed in the presence of anti-IP 10 antibodies of the present invention by using a transwell plate.
Figure 9B:
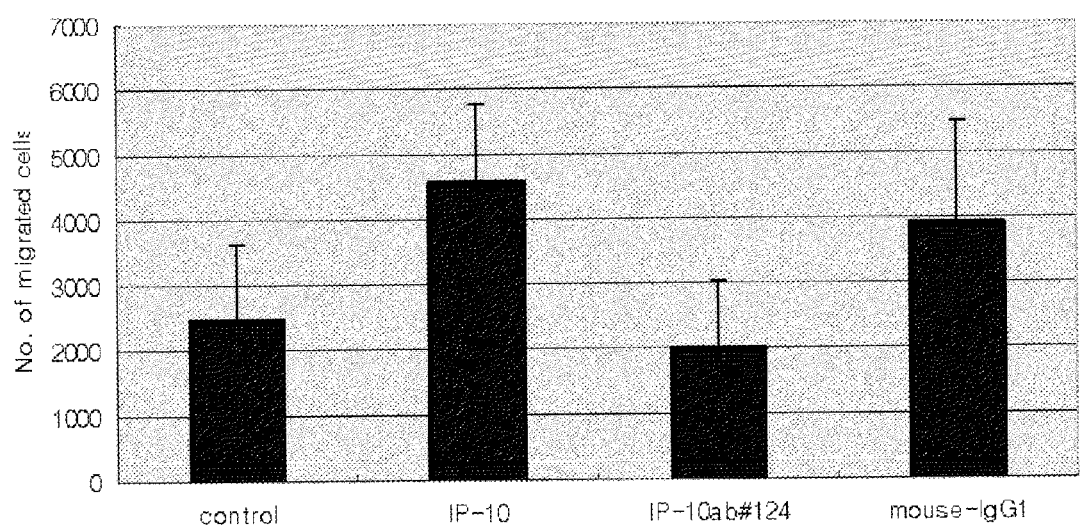
Figure 9C:
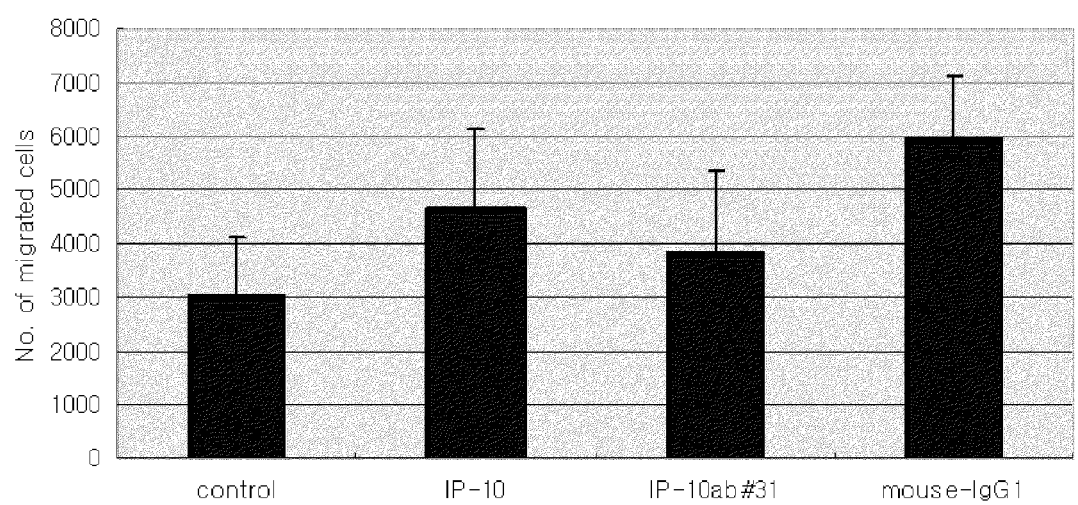

In addition, the anti-IP-10 antibodies of the present invention inhibited the migration of $CD4^+$ T cells in response to IP-10 as represented FIGS. 9A-9C.

Discussion

Osteoclasts, which originate from hematopoietic cells, are bone-resorbing cells that have been shown to be regulated through several distinct processes, including proliferation, fusion, and maturation. Chronic inflammation in the circumference of the bone causes excessive osteoclast formation, which in turn causes bone erosion in vivo. Inflammatory cytokines produced by macrophages and lymphocytes at sites of inflammation play an important role in bone-related diseases such as RA.[6,16] The regulation of osteoclast formation induced by inflammatory cytokines is vital for preventing inflammation-induced bone loss. Although the mechanism of osteoclast differentiation is well known, how osteoclast precursors or osteoclasts are recruited into bone tissue is not well known.

The recruitment of osteoclast precursors into bone tissues is regulated by various chemokines, such as SDF-1α and MIP-1α.[31,32] Chemokines are chemoattractant cytokines that play an important role in the pathogenesis of inflammatory disease, such as RA, periodontal disease, and inflammatory bowel disease, through recruitment of inflammatory cells to sites of inflammation.[33,35] In particular, it has been reported that many chemokines, including IL-8, GROα, IP-10, MIG, MCP-1, and fractalkine, are abundantly increased in RA compared with osteoarthritis.[36] Chemokines can induce the production of metalloproteinases and cytokines, leukocyte activation, and the proliferation of several cell types.[8,31] The antagonist of CXCR4 reduces CIA progression by inhibiting macrophage recruitment to inflamed joints.[37] Fractalkine may contribute to the recruitment of macrophages and $CD4^+$ T cells into the synovium in CIA. Bone erosion in the synovium is inhibited by antibody to fractalkine.[33] Also, IP-10 is expressed in several diseases, including inflammatory skin disease, in the lungs of HIV-infected patients, in patients with systemic lupus erythematosus, and in patients with chronic hepatitis.[38-41]

We found that IP-10 is increased in inflamed joints in a mouse model of CIA and is increased in serum and synovial fluid in patients with RA (FIG. 1), which suggests that IP-10 plays an important role in the progression of RA. Postmenopausal. osteoporosis is a predominant bone disease that is caused by increased bone resorption resulting from a complete deficiency of estrogen rather than inflammation. Thus, we examined serum concentrations of IP-10 in osteoporosis patients, but found that these were not elevated compared with concentrations in healthy humans (data not shown). These results show that the up-regulation of IP-10 is involved in bone diseases such as RA that are mediated by inflammation.

IP-10 is expressed in the synovium in RA and is increased by the coculture of synoviocytes and monocytes in vitro. However, the induction of IP-10 in monocytes is not reduced by the addition of antibodies against IFN-γ or TNF-α.[24] Although many studies have reported that IP-10 is mainly secreted by monocytes and macrophages in response to IFN-γ, LPS, and TNF-α, IFN-γ is not expressed in the synovial tissue or fluid in RA,[42] and has a robust inhibitory effect on osteoclast differentiation.[43] Therefore, it is hard to define exactly how IP-10 is induced in the synovium in RA.

It is well known that IFN-γ mediates MIG expression in various cell types. Although MIG is expressed in IFN-γ-treated cells, we showed previously that MIG is induced by RANKL and in turn induces the migration of osteoclast precursors and osteoclasts.[26] Also, MIG was shown to be increased in the synovial fluid of RA patients.[36] RANKL is expressed in synovial tissue, synovial fibroblasts, chondrocytes, and mesenchymal cells in the cartilage as well as in osteoblasts and activated T cells.[44] Therefore, we examined the ability of RANKL to regulate the expression of IP-10. RANKL significantly induced IP-10 expression in osteoclast precursors (FIG. 3). These results strongly suggest that RANKL is associated with IP-10 secretion in the synovium of inflamed joints.

The accumulation of monocytes, macrophages, and lymphocytes in the synovium in response to various chemokines is important in the initiation of RA. Inflammatory cytokines such as IL-1, TNF-α, and IL-6 are important inflammatory mediators that have been shown to be involved in the pathogenesis of RA.[45] In the context of RA, bone-resorbing osteoclasts are differentiated from osteoclast precursors and immature osteoclasts exposed to inflammatory cytokines such as RANKL, TNF-α, IL-1, and IL-17, which are expressed by activated T cells ($CD4^+$) and by macrophages in the inflamed joints.[46] In particular, TNF-α is a multifunctional cytokine that is mainly expressed by activated macrophages; it causes the production of other cytokines, including IL-1, IL-6, and RANKL. Inappropriate expression of TNF-α affects a wide range of inflammatory disorders, including Crohn disease and psoriatic arthritis.[47,48]

Figure 5:
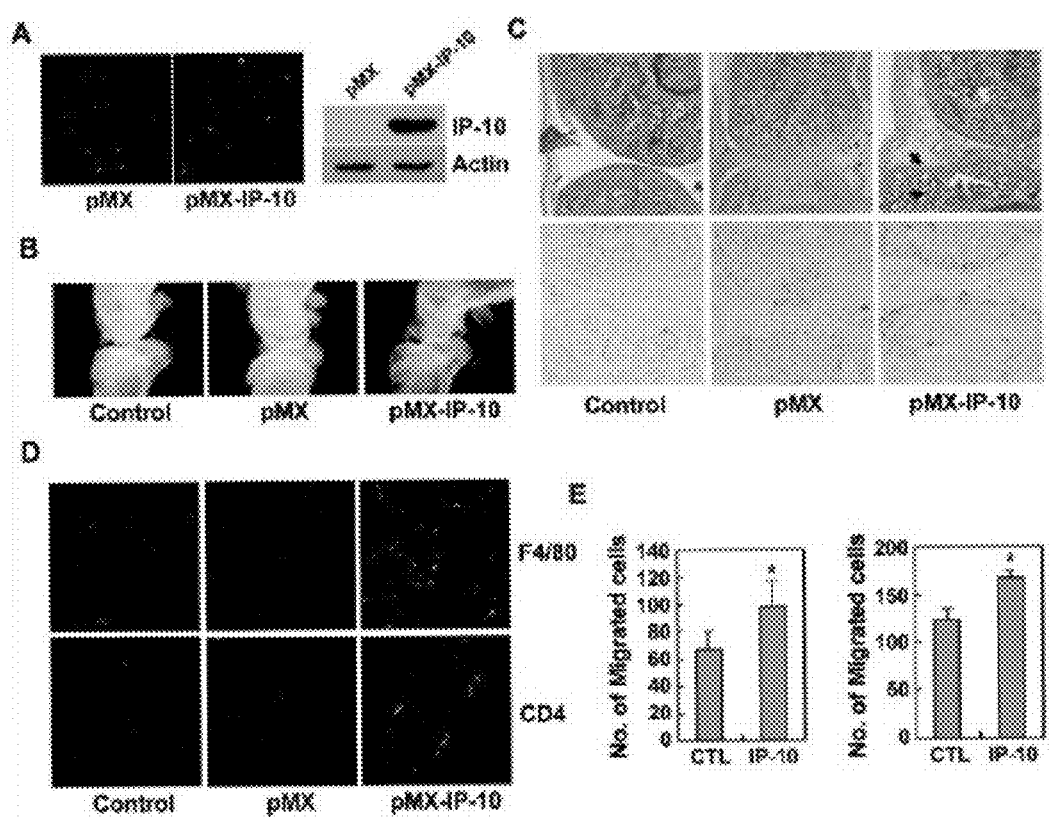
FIGS. 5A-5E. IP-10 can promote bone erosion in vivo. pMX-IRES-EGFP or pMX-IP-10-IRES-EGFP DNA was transiently transfected into Plat E cells to obtain retroviruses. 48 h after transfection, media containing retroviruses were collected. (A) Osteoclast precursors were infected with control or IP-10 retroviruses for 48 h in the presence of M-CSF (30 ng/ml) and polybrene (6 µg/ml). Cells were fixed, mounted, and visualized with a confocal microscope or analyzed by Western blotting with antibody to IP-10. (B) The mice were injected with either control or IP-10 retroviruses (50 µl) in the tibial metaphysis once a week for 6 weeks. Mice were sacrificed at 6 wk, and radiographs were taken with a soft X-ray machine. (C) Sections of the joints were stained with H&E (top) or TRAP (bottom). Arrows indicate bone erosion. (D) CD4+ and F4/80+ cells were immunostained with antibody for CD4 or F4/80, respectively. (E) The migration of CD4+ T cells (left) and osteoclast precursors (right) in response to IP-10 was analyzed by using a transwell plate. Values were indicated as the mean±SD. *Significant difference between control and IP-10 (P<0.05).

The mouse model of CIA that we used has pathologic features similar to those in human patients with RA. Enhanced levels of TNF-α play a critical role in inflammation and mediate cartilage and bone destruction in CIA.[49] Consistent with previous reports, in the present study, serum concentrations of TNF-α and RANKL were greatly elevated in the CIA mice, but the up-regulation of TNF-α and RANKL was inhibited by neutralizing antibody to IP-10, which also suppressed the infiltration of $F4/80^+$ macrophages and $CD4^+$ T cells into inflamed joints (FIG. 2). We also showed that IP-10 mediates the recruitment of $F4/80^+$ macrophages and $CD4^+$ T cells into bone (FIG. 5). Our results strongly suggest a critical role for IP-10 in the infiltration of $F4/80^+$ macrophages and $CD4^+$ T cells into the synovium and in the regulation of TNF-α and RANKL.

Activated, but not naïve, T cells express RANKL; IFN-γ is also expressed in T cells. Activated T cells can induce osteoclast formation in vitro and in vivo.[27] Although IFN-γ-producing T cells induce osteoclast differentiation, IFN-γ-non-producing T cells do not.[50] Surprisingly, IFN-γ promotes osteoclast differentiation in a culture of peripheral blood mononuclear cells from osteopetrotic patients and mediates bone resorption in vivo.[51] A recent study reported a potential role of T cells in a mouse model of estrogen deficiency.[52] In that study, T cell-deficient mice (nude mice) failed to develop osteoporosis by estrogen deficiency, but bone erosion was caused by the administration of T cells.[52] These results imply that T cells may be important for bone erosion in pathologic conditions.

Figure 4:
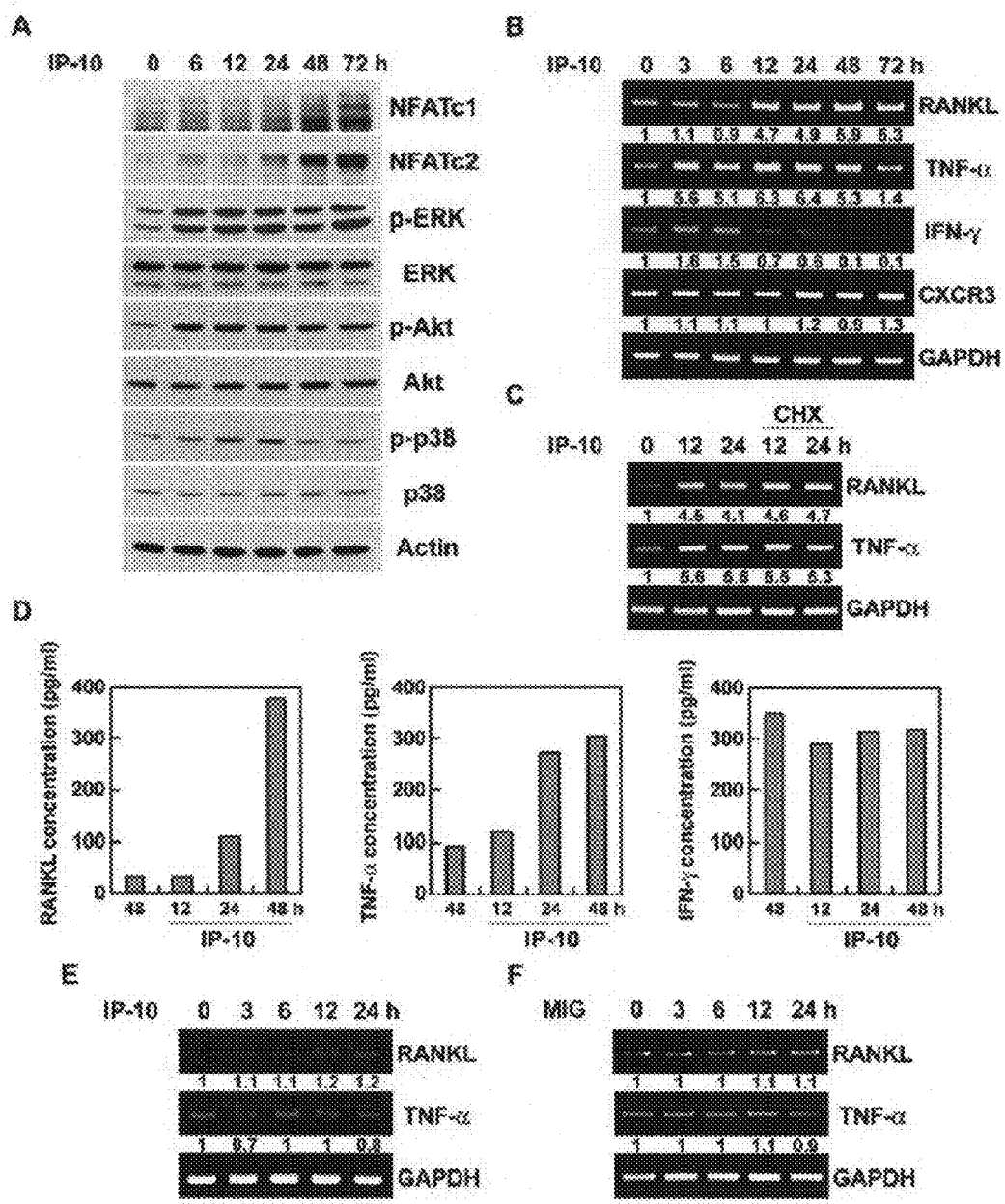
FIG. 4. IP-10 activates CD4+ T cells and induces osteoclastogenic cytokines. (A) Activated CD4+ T cells were positively selected by using anti-CD4 magnetic beads and were stimulated with IP-10 (100 ng/ml) for the indicated time. Cell lysates were analyzed by Western blotting with antibodies for NFATc1, NFATc2, phospho-ERK, ERK, phospho-Akt, Akt, phospho-p38, p38, and actin. (B) Activated CD4+ T cells were stimulated as in (A). The mRNA expression levels of the indicated genes were analyzed by RT-PCR. Densitometric values for each band were quantified by densitometric analysis and were normalized to the GAPDH intensity. (C) Activated CD4+ T cells were pretreated with or without cyclohex- imide (CHX; 3 µg/ml) for 30 min before the addition of IP-10 (100 ng/ml) and were further stimulated with IP-10 (100 ng/ml) for the indicated time. (D) Activated CD4+ T cells were stimulated with IP-10 (100 ng/ml) for the indicated time. The culture medium was collected, and concentrations of RANKL (left), TNF-α (middle), and IFN-γ (right) were analyzed by ELISA. (E) CD8+ T cells were purified as in (A). CD8+ T cells were stimulated for the indicated times. The mRNA expression levels of the indicated genes were analyzed by RT-PCR. (F) Activated CD4+ T cells were stimulated with MIG (100 ng/ml) for the indicated times. RT-PCR was as above.

Previous reports showed that synovial T cells express RANKL, and that RANKL is only expressed in T cells in the synovium in RA and not in synovial fibroblasts.[53,54] However, other reports showed that RANKL is expressed in synovial fibroblasts and synovial tissue, but at lower levels than in T cells.[16] We also found that RANKL is expressed in synovial fibroblasts from RA patients. Thus, we examined the effect of IP-10 in RANKL or TNF-α expression in synovial fibroblasts and macrophages, which are resident in the synovium and play an important role in inflammation in the inflamed joints. IP-10 did not induce the expression of RANKL or TNF-α in synovial fibroblasts and macrophages (data not shown). These results suggest that IP-10 specifically activates $CD4^+$ T cells only to promote increased expression of RANKL and TNF-α in the inflamed joints. In the present study, we showed that IP-10 mediates the induction of NFATc1 and NFATc2 and stimulates sustained ERK and Akt phosphorylation (FIG. 4). The induction of the NFAT family of transcription factors leads to the activation and function of T cells and mediates the expression of various cytokines, such as IL-2, IFN-γ, TNF-α, and RANKL.[27,55] Induction of RANKL in activated T cells is regulated by PKC, PI-3K, ERK, and calcineurin signaling pathways. RANKL expression is 10-fold higher in $CD4^+$ T cells than in $CD8^+$ T cells.[16] We showed that IP-10 significantly induces osteoclast differentiation in a coculture of osteoclast precursors and $CD4^+$ T cells by inducing RANKL in $CD4^+$ T cells. These results show that synovial T cell production of RANKL plays a critical role in osteoclast formation in RA. In addition, similar to CD40 ligand, T cell-derived RANKL in the immune system is important for promoting $CD4^+$ T cell proliferation and mediates the survival of dendritic cells through interaction with RANK.[6]

We provide strong evidence that RANKL promotes the expression of IP-10 in osteoclast precursors, and that IP-10 mediates RANKL expression in T cells ($CD4^+$) in the synovium. The reciprocal cross-talk between RANKL and IP-10 is responsible for inflammation and bone erosion by recruiting $CD4^+$ T cells and macrophages in the synovium. IP-10 might be one of the therapeutic targets in bone diseases. Blockade of IP-10, in particular, by use of antibodies to IP-10 may be an important armamentarium in the prevention and treatment of bone destruction in bone diseases.

Having described a preferred embodiment of the present invention, it is to be understood that variants and modifications thereof falling within the spirit of the invention may become apparent to those skilled in this art, and the scope of this invention is to be determined by appended claims and their equivalents.

References

1. Teitelbaum S L, Ross F R Genetic regulation of osteoclast development and function. Nat Rev Genet. 2003;4:638-649.
2. Boyle W J, Simonet W S, Lacey D L. Osteoclast differentiation and activation. Nature. 2003;423:337-342.
3. Krane S M. Identifying genes that regulate bone remodeling as potential therapeutic targets. J Exp Med. 2005;201:841-843.
4. Udagawa N, Takahashi N, Yasuda H, et al. Osteoprotegerin produced by osteoblasts is an important regulator in osteoclast development and function. Endocrinology. 2000;141:3478-3484.
5. Rodan G A, Martin T J. Therapeutic approaches to bone diseases. Science. 2000;289:1508-1514.
6. Theill L E, Boyle W J, Penninger J M. RANK-L and RANK: T cells, bone loss. Annu Rev Immunol. 2002;20:795-823.
7. Murphy P M, Baggiolini M, Charo I F, et al. International union of pharmacology, XXII: nomenclature for chemokine receptors. Pharmacol Rev. 2000;52:145-176.
8. Rossi D, Zlotnik A. The biology of chemokines and their receptors. Annu Rev Immunol. 2000;18:217-242.
9. Bendre M S, Montague D C, Peery T, Akel N S, Gaddy D, Suva L J. Interleukin-8 stimulation of osteoclastogenesis and bone resorption is a mechanism for the increased osteolysis of metastatic bone disease. Bone. 2003;33:28-37.
10. Wright L M, Maloney W, Yu X, Kindle L, Collin-Osdoby P, Osdoby P. Stromal cell-derived factor-1 binding to its chemokine receptor CXCR4 on precursor cells promotes the chemotactic recruitment, development and survival of human osteoclasts. Bone. 2005;36:840-853.
11. Abe M, Hiura K, Wilde J, et al. Role for macrophage inflammatory protein (MIP)-1alpha and MIP-1beta in the development of osteolytic lesions in multiple myeloma. Blood. 2002;100:2195-2202.
12. Luster A D, Ravetch J V. Biochemical characterization of a gamma interferon-inducible cytokine (IP-10). J Exp Med. 1987;166:1084-1097.
13. Ohmori Y, Hamilton T A. Cooperative interaction between interferon (IFN) stimulus response element and kappa B sequence motifs controls IFN gamma- and lipopolysaccharide-stimulated transcription from the murine IP-10 promoter. J Biol Chem. 1993;268:6677-6688.
14. Taub D D, Lioyd A R, Conlon K, et al. Recombinant human interferon-inducible protein 10 is a chemoattractant for human monocytes and T lymphocytes and promotes T cell adhesion to endothelial cells. J Exp Med. 1993;177:1809-1814.
15. Jinquan T, Jing C, Jacobi H H, et al. CXCR3 expression and activation of eosinophils: role of IFN-gamma-inducible protein-10 and monokine induced by IFN-gamma. J Immunol. 2000;165:1548-1556.
16. O'Gradaigh D, Compston J E. T-cell involvement in osteoclast biology: implications for rheumatoid bone erosion. Rheumatology. 2004;43:122-130.
17 Nanki T, Hayashida K, El-Gabalawy, et al. Stromal cell-derived factor-1-CXC chemokine receptor 4 interactions play a central role in CD4+ T cell accumulation in rheumatoid arthritis synovium. J. Immunol. 2000;165:6590-6598.
18. Ji H, Pettit A, Ohmura K, et al. Critical roles for interleukin 1 and tumor necrosis factor alpha in antibody-induced arthritis. J Exp Med. 2002;196:77-85.
19. Kotake S, Udagawa N, Takahashi N, et al. IL-17 in synovial fluids from patients with rheumatoid arthritis is a potent stimulator of osteoclastogenesis. J Clin Invest. 1999;103:1345-1352.
20. Dufour J H, Dziejman M, Liu M T IFN-gamma-inducible protein 10 (IP-10; CXCL10)-deficient mice reveal a role for IP-10 in effector T cell generation and trafficking. J Immunol. 2002;168:3195-3204.

21. Sorensen T L, Tani M, Jensen J, et al. Expression of specific chemokines and chemokine receptors in the central nervous system of multiple sclerosis patients. J Clin Invest. 1999;103:807-815.
22. Mach F, Sauty A, Iarossi A S, et al. Differential expression of three T lymphocyte-activating CXC chemokines by human atheroma-associated cells. J Clin Invest. 1999;104:1041-1050.
23. Iijima W, Ohtani H, Nakayama T, et al. Infiltrating CD8+T cells in oral lichen planus predominantly express CCR5 and CXCR3 and carry respective chemokine ligands RANTES/CCL5 and IP-10/CXCL10 in their cytolytic granules: a potential self-recruiting mechanism. Am J Pathol. 2003;163:261-268.
24. Hanaoka R, Kasama T, Muramatsu M, et al. A novel mechanism for the regulation of IFN-γ inducible protein-10 expression in rheumatoid arthritis. Arthritis Res Ther. 2003;5:R74-81.
25. Kwak H B, Lee S W, Li Y J, et al. Inhibition of osteoclast differentiation and bone resorption by a novel lysophosphatidylcholine derivative, SCOH. Biochem Pharmacol. 2004;67:1239-1248.
26. Kwak H B, Lee S W, Jin H M, et al. Monokine induced by interferon-gamma is induced by receptor activator of nuclear factor kappa B ligand and is involved in osteoclast adhesion and migration. Blood. 2005;105:2963-2969.
27. Kong Y Y, Feige U, Sarosi I, et al. Activated T cells regulate bone loss and joint destruction in adjuvant arthritis through osteoprotegerin ligand. Nature. 1999;402:304-309.
28. Faber J M. Mig and IP-10: CXC chemokines that target lymphocytes. J Leukoc Biol. 1997;61:246-257.
29. Kwak H B, Jin H M, Ha H, et al. Tumor necrosis factor-alpha induces differentiation of human peripheral blood mononuclear cells into osteoclasts through the induction of p21(WAF1/Cip1). Biochem Biophys Res Commun. 2005;330:1080-1086.
30. Lam J, Takeshita S, Barker J E, et al. TNF-alpha induces osteoclastogenesis by direct stimulation of macrophages exposed to permissive levels of RANK ligand. J Clin Invest. 2000;106:1481-1488.
31. Yu X, Huang Y, Collin-Osdoby P, Osdoby R Stromal cell-derived factor-1 (SDF-1) recruits osteoclast precursors by inducing chemotaxis, matrix metalloproteinase-9 (MMP-9) activity, and collagen transmigration. J Bone Miner Res. 2003;18:1404-1418.
32. Toh K, Kukita T, Wu Z, Et al. Possible involvement of MIP-1alpha in the recruitment of osteoclast progenitors to the distal tibia in rats with adjuvant-induced arthritis. Lab Invest. 2004;84:1092-1102.
33. Nanki T, Urasaki Y, Imai T, et al. Inhibition of fractalkine ameliorates murine collagen-induced arthritis. J Immunol. 2004;173:7010-7016.
34. Hosokawa Y, Nakanishi T, Yamaguchi D, et al. Macrophage inflammatory protein 3alpha-CC chemokine receptor 6 interactions play an important role in CD4+ T-cell accumulation in periodontal diseased tissue. Clin Exp Immunol. 2002;128:548-554.
35. Vogel J D, West G A, Danese S, et al. CD40-mediated immune-nonimmune cell interactions induce mucosal fibroblast chemokines leading to T-cell transmigration. Gastroenterology. 2004;126:63-80.
36. Koch A E. Chemokines and their receptors in rheumatoid arthritis: future targets? Arthritis Rheum. 2005;52:710-721.
37. Matthys P, Hatse S, Vermeire K, et al. AMD3100, a potent and specific antagonist of the stromal cell-derived factor-1 chemokine receptor CXCR4, inhibits autoimmune joint inflammation in IFN-gamma receptor-deficient mice. J Immunol. 2001;167:4686-4692.
38. Flier J, Boorsma D M, van Beek P J, et al. Differential expression of CXCR3 targeting chemokines CXCL10, CXCL9, and CXCL11 in different types of skin inflammation. J Pathol. 2001;194:398-405.
39. Agostini C, Facco M, Siviero M, et al. CXC chemokines IP-10 and mig expression and direct migration of pulmonary CD8+/CXCR3+ T cells in the lungs of patients with HIV infection and T-cell alveolitis. Am J Respir Crit Care Med. 2000;162:1466-1473.
40. Eriksson C, Eneslatt K, Ivanoff J, Rantapaa-Dahlqvist S, Sundqvist K G. Abnormal expression of chemokine receptors on T-cells from patients with systemic lupus erythematosus. Lupus. 2003;12:766-774.
41. Narumi S, Tominaga Y, Tamaru M, et al. Expression of IFN-inducible protein-10 in chronic hepatitis. J Immunol. 1997;158:5536-5544.
42. Fox D A. The role of T cells in the immunopathogenesis of rheumatoid arthritis: new perspectives. Arthritis Rheum. 1997;40:598-609.
43. Takayanagi H, Ogasawara K, Hida S, et al. T-cell-mediated regulation of osteoclastogenesis by signalling cross-talk between RANKL and IFN-gamma. Nature. 2000;408:600-605.
44. Neumann E; Gay S, Muller-Ladner U. The RANK/RANKL/osteoprotegerin system in rheumatoid arthritis: new insights from animal models. Arthritis Rheum. 2005;52:2960-2967.
45. Barrera P, Joosten L A, den Broeder A A, et al. Effects of treatment with a fully human anti-tumour necrosis factor alpha monoclonal antibody on the local and systemic homeostasis of interleukin 1 and TNF alpha in patients with rheumatoid arthritis. Ann Rheum Dis. 2001;60:660-669.
46. Udagawa N, Kotake S, Kamatani N, Takahashi N, Suda T. The molecular mechanism of osteoclastogenesis in rheumatoid arthritis. Arthritis Res. 2002; 4:281-289.
47. Targan S R, Hanauer S B, van Deventer S J, et al. A short-term study of chimeric monoclonal antibody cA2 to tumor necrosis factor-α for Crohn's disease. N Engl J Med. 1997;337:1029-1035.
48. Danning C L, Illei G G, Hitchon C, et al. Macrophage-derived cytokine and nuclear factor kappa B p65 expression in synovial membrane and skin of patients with psoriatic arthritis. Arthritis Rheum. 2000;43:1244-1256.
49. Ehrenstein M R, Evans J G, Singh A, et al. Compromised function of regulatory T cells in rheumatoid arthritis and reversal by anti-TNF-α therapy. J Exp Med. 2004;200:277-285.
50. Kotake S, Nanke Y, Mogi M, et al. IFN-gamma-producing human T cells directly induce osteoclastogenesis from human monocytes via the expression of RANKL. Eur J Immunol. 2005;35:3353-3363.
51. Madyastha P R, Yang S, Ries W L, Key L L, Jr. IFN-enhances osteoclast generation in cultures of peripheral blood from osteoporotic patients and normalizes superoxide production. J Interferon Cytokine Res. 2000;20:645-652.
52. Cenci S, Weitzmann M N, Roggia C, et al. Estrogen deficiency induces bone loss by enhancing T-cell production of TNF-alpha. J Clin Invest. 2000;106:1229-1237.

53. Gravallese E M, Manning C, Tsay A, et al. Synovial tissue in rheumatoid arthritis is a source of osteoclast differentiation factor. Arthritis Rheum. 2000;43:250-258.
54. Kotake S, Udagawa N, Hakoda M, et al. Activated human T cells directly induce osteoclastogenesis from human monocytes: possible role of T cells in bone destruction in rheumatoid arthritis patients. Arthritis Rheum. 2001;44: 1003-1012.
55. Chen J, Amasaki Y, Kamogawa Y, et al. Role of NFATx (NFAT4/NFATc3) in expression of immunoregulatory genes in murine peripheral CD4+ T cells. J Immunol. 2003; 170:3109-3117.

---

What is claimed is:

1. A method for inhibiting the expression of RANKL (receptor activator of NF-κB ligand), which comprises administering to a subject a pharmaceutical composition comprising (a) a pharmaceutically effective amount of an antibody to IP-10 (interferon-γ-inducible protein 10); and (b) a pharmaceutically acceptable carrier, wherein the antibody to IP-10 is a monoclonal antibody produced by a hybridoma cell line as deposited with the Korean Cell Line Research Foundation under Accession No. KCLRF-BP-00142, KCLRF-BP-00143, KCLRF-BP-00144, or KCLRF-BP-00145.

2. The method according to claim 1, wherein the antibody to IP-10 inhibits the expression of TNF-α(tumor necrosis factor-α).

3. The method according to claim 1, wherein the antibody to IP-10 is a monoclonal antibody produced by a hybridoma cell line as deposited with the Korean Cell Line Research Foundation under Accession Nos. KCLRF-BP-00142 or KCLRF-BP-00144.

4. The method according to claim 1, wherein the method treats a bone disease characterized by bone erosion due to increased osteoclast activity and inflammation by inhibiting the expression of RANKL.

5. The method according to claim 4, wherein the bone disease is osteoporosis, juvenile osteoporosis, osteogenesis imperfecta, hypercalcemia, hyperparathyroidism, osteomalacia, osteohalisteresis, osteolytic bone disease, osteonecrosis, Paget's disease of bone, bone loss due to rheumatoid arthritis, inflammatory arthritis, osteomyelitis, metastatic bone diseases, periodontal bone loss, bone loss due to cancer and age-related loss of bone mass.

* * * * *

SEQUENCE LISTING

```
<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct

<400> SEQUENCE: 1
caggtttgca ggactcgac                                                   19

<210> SEQ ID NO 2
<211> LENGTH: 19
<212> TYPE: DNA
<213> ORGANISM: Artificial Sequence
<220> FEATURE:
<223> OTHER INFORMATION: Synthetic Construct

<400> SEQUENCE: 2
agcagggaag ggttggaca                                                   19

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3
acaccgtcag ccgatttgc                                                   19

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4
ccctgagcca taatcccctt t                                                21

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
gtttgaggtc aacaacccac                                                  20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct
```

-continued

```
<400> SEQUENCE: 6
aatctgagtt cagtcagccg                                              20

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
gccacccatt gccagtacaa c                                            21

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct

<400> SEQUENCE: 8
tcccacaaag gcatagagca gc                                           22

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
aagcctcccc atcagcacca                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
tgtccatcca tcgcagcacc                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
caaggctgtg ggcaaggtca                                              20

<210> SEQ ID NO 12
<211> LENGTH: 23
<212> TYPE: DNA
<213> ORGANISM: Artificial Sequence
<220> FEATURE:
<223> OTHER INFORMATION: Synthetic Construct

<400> SEQUENCE: 12
aggtggaaga gtgggagttg ctg                                          23
```